United States Patent
Rivard

(10) Patent No.: US 7,118,524 B2
(45) Date of Patent: Oct. 10, 2006

(54) DOSIMETRY FOR CALIFORNIUM-252 ($^{252}$CF) NEUTRON-EMITTING BRACHYTHERAPY SOURCES AND ENCAPSULATION, STORAGE, AND CLINICAL DELIVERY THEREOF

(75) Inventor: Mark J. Rivard, Hopkinton, MA (US)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 10/420,184

(22) Filed: Apr. 22, 2003

(65) Prior Publication Data

US 2003/0204126 A1 Oct. 30, 2003

Related U.S. Application Data

(62) Division of application No. 09/641,356, filed on Aug. 17, 2000, now Pat. No. 6,551,232.

(60) Provisional application No. 60/149,816, filed on Aug. 19, 1999.

(51) Int. Cl.
*A61N 5/00* (2006.01)
*A61B 6/00* (2006.01)
(52) U.S. Cl. .............................................. 600/3; 600/8
(58) Field of Classification Search .................. 600/1–8
See application file for complete search history.

(56) References Cited

U.S. PATENT DOCUMENTS

| | | | |
|---|---|---|---|
| 4,362,940 A | | 12/1982 | Almond |
| 4,510,924 A | * | 4/1985 | Gray ........................ 424/1.61 |
| 4,784,116 A | * | 11/1988 | Russell et al. ................ 600/8 |
| H669 H | | 9/1989 | Fairchild et al. |
| 5,341,292 A | | 8/1994 | Zamenhof |
| 5,776,114 A | | 7/1998 | Frantzen et al. |
| 5,833,593 A | | 11/1998 | Liprie |
| 6,267,717 B1 | | 7/2001 | Stoll et al. |
| 6,352,500 B1 | * | 3/2002 | Halpern ........................ 600/3 |

FOREIGN PATENT DOCUMENTS

| | | | | |
|---|---|---|---|---|
| GE | 2314798 | * | 4/1973 | .................... 600/8 |
| WO | WO 94/25106 | | 11/1994 | |

OTHER PUBLICATIONS

R. Nath et al., *Dosimetry of interstitial brachytherapy sources: Recommendations of the AAPM Radiation Therapy Committee Task Group No. 43*. Med. Phys., vol. 22, No. 2, pp. 209-234 (1995).

M. J. Rivard, *Neutron dosimetry, moderated energy spectrum, and neutron capture therapy for $^{252}$Cf medical sources*. Med. Phys., vol. 26, No. 3, pp. 495 (1999).

M. J. Rivard, *Dosimetry for $^{252}$Cf neutron emitting brachytherapy sources: Protocol, measurements, and calculations*. Med. Phys., vol. 26, No. 8, pp. 1503-1514 (1999).

(Continued)

*Primary Examiner*—Samuel G. Gilbert
(74) *Attorney, Agent, or Firm*—Shane H. Hunter, Esq.; Mintz, Levin, Cohn, Ferris, Glovsky and Popeo, P.C.

(57) ABSTRACT

The present invention discloses a methodology for the characterization and determination of mixed-field dosimetry for $^{252}$Cf Applicator Tube (AT)-type medical sources, utilizing ionization chambers, GM counters, and Monte Carlo methods. Unlike the previous methodologies, the present invention discloses a specification of dose to muscle, rather than dose to water, for clinical dosimetry of $^{252}$Cf medical sources. A dosimetry protocol, similar to that utilized for ICRU-45, with parameters determined specifically for $^{252}$Cf brachytherapy is disclosed. Neutron isodose distributions and data necessary for clinical implementation of $^{252}$Cf AT sources are also disclosed herein. Additionally, novel methods for the encapsulation, storage, and delivery/implantation of $^{252}$Cf radionuclide sources are disclosed.

29 Claims, 11 Drawing Sheets

OTHER PUBLICATIONS

V. N. Ivanov, et al., *Dosimetry of Cf-252 Radiation: Studies in the USSR*. Nuclear Science Applications, vol. 2, pp. 291-299, (1986).

M. J. Rivard et al., *Clinical brachytherapy with neutron emitting $^{252}Cf$ sources and adherence to AAPM TG-43 dosimetry protocol*. Med. Phys., vol. 26, No. 1, pp. 87-96 (1999).

Y. A. Karelin et al., *Californium-252 Neutron Sources*. Appl. Radiat. Isot. vol. 48, No. 10-12, pp. 1563-1566 (1997).

R. C. Martin et al., *Development of High-activity $^{252}Cf$ Sources for Neutron Brachytherapy*. Appl. Radiat. Isot. vol. 48, No. 10-12, pp. 1567-1570 (1997).

ICRU Report No. 45, *Clinical Neutron Dosimetry, Part 1: Determination of Absorbed Dose in a Patient Treated by External Beams of Fast Neutrons*, International Commission on Radiation Units and Measurements, Issue Nov. 15, 1989.

AAPM Report No. 43, *Quality Assessment and Improvement of Dose Response Models: Some Effects of Study Weaknesses on Study Findings. "C'Est Magnifique?"*, Published for the American Association of Physics Publishing, Jun. 15, 1993.

A. Wambersie et al., *Present Status, Trends and Needs in Fast Neutron Therap*, Buletin Du Cancer/Radiotherapie, 83/Suppl. vol. 1, pp. 68S-77S, 1996.

* cited by examiner

| MJR | variSource | geometry | factor | MCNP | run |
|---|---|---|---|---|---|
| 1 | 0 | -1 | -2 3 | | |
| 2 | 0 | -1 | 2 -900 | | |
| 3 | 0 | -1 | -3 -900 | | |
| 4 | 0 | 1 | -900 -111 | | |
| 5 | 0 | 111 | -161 -200 | 201 -300 | 301 |
| 900 | 0 | 161 | -900 -200 | 201 -300 | 301 |
| 901 | 0 | | -900 -200 | 111 300 | |
| 902 | 0 | | -900 200 | 111 301 | |
| 903 | 0 | | -900 201 | 111 -301 | |
| 904 | 0 | | -900 -201 | 111 -300 | |
| 999 | 0 | | 900 | | |

| | | |
|---|---|---|
| 1 | cx | 0.017 |
| 2 | px | 0.5 |
| 3 | px | -0.5 |
| 900 | so | 0.55 |
| 111 | pz | 0.017 |
| 112 | pz | 0.02 |
| 113 | pz | 0.03 |
| 114 | pz | 0.04 |
| 115 | pz | 0.05 |
| 116 | pz | 0.06 |
| 117 | pz | 0.07 |
| 118 | pz | 0.08 |
| 119 | pz | 0.09 |
| 120 | pz | 0.10 |
| 121 | pz | 0.11 |
| 122 | pz | 0.12 |
| 123 | pz | 0.13 |
| 124 | pz | 0.14 |
| 125 | pz | 0.15 |
| 126 | pz | 0.16 |
| 127 | pz | 0.17 |
| 128 | pz | 0.18 |
| 129 | pz | 0.19 |
| 130 | pz | 0.20 |
| 131 | pz | 0.21 |
| 132 | pz | 0.22 |
| 133 | pz | 0.23 |
| 134 | pz | 0.24 |
| 135 | pz | 0.25 |
| 136 | pz | 0.26 |
| 137 | pz | 0.27 |
| 138 | pz | 0.28 |
| 139 | pz | 0.29 |
| 140 | pz | 0.30 |
| 141 | pz | 0.31 |
| 142 | pz | 0.32 |
| 143 | pz | 0.33 |
| 144 | pz | 0.34 |
| 145 | pz | 0.35 |
| 146 | pz | 0.36 |
| 147 | pz | 0.37 |
| 148 | pz | 0.38 |
| 149 | pz | 0.39 |
| 150 | pz | 0.40 |
| 151 | pz | 0.41 |
| 152 | pz | 0.42 |
| 153 | pz | 0.43 |
| 154 | pz | 0.44 |
| 155 | pz | 0.45 |
| 156 | pz | 0.46 |
| 157 | pz | 0.47 |
| 158 | pz | 0.48 |
| 159 | pz | 0.49 |
| 160 | pz | 0.50 |
| 161 | pz | 0.51 |
| 200 | px | 0.005 |
| 201 | px | -0.005 |
| 300 | py | 0.005 |
| 301 | py | -0.005 |

```
MODE   p
IMP:p  1 9r 0
SDEF   par=2 cel=1 pos=0 0 0 rad=d2 ext=d3 axs 1 0 0
SI2    0  0.017
SI3    -0.5  0.5
F4:p   5
FS4    160 48i 112
nps    1e9
prdmp  3j 2
```

FIG. 3

DOSIMETRY FOR CALIFORNIUM-252 ($^{252}$CF) NEUTRON-EMITTING BRACHYTHERAPY SOURCES AND ENCAPSULATION, STORAGE, AND CLINICAL DELIVERY THEREOF

RELATED APPLICATIONS

The present application is a divisional of, and claims the benefit of, U.S. application Ser. No. 09/641,356, now U.S. Pat. No. 6,551,232, filed on Aug. 17, 2000, entitled "DOSIMETRY FOR CALIFORNIUM-252 ($^{252}$Cf) NEUTRON-EMITTING BRACHYTHERAPY SOURCES AND ENCAPSULATION, STORAGE, AND CLINICAL DELIVERY THEREOF," which claims priority to, and the benefit of, U.S. Provisional Application Ser. No. 60/149,816, filed on Aug. 19, 1999, entitled "DOSIMETRY FOR CALIFORNIUM-252 ($^{252}$Cf) NEUTRON-EMITTING BRACHYTHERAPY SOURCES", whose disclosure is incorporated herein by reference in its entirety.

FIELD OF THE INVENTION

The present invention relates to devices and methods for utilization in brachytherapy in the fields of medical physics and therapeutic radiology. More specifically, the present invention relates to brachytherapy dosimetric protocols utilizing the neutron-emitting radioisotope californium-252 ($^{252}$Cf), as well as $^{252}$Cf encapsulation, storage, and remote delivery (afterloading) methodologies.

BACKGROUND OF THE INVENTION

I. Brachytherapy

Radiation therapy refers to the treatment of diseases with ionizing radiation. Of particular interest is the treatment of neoplastic disease, especially solid, malignant tumors. In radiation therapy, the goal is to destroy the malignant tissue while concomitantly minimizing the exposure of medical personnel to radiation and minimizing radiation damage to other tissue, such as nearby healthy tissue. The recognized method employed for radiation treatment in body cavities (e.g., the throat, bowel or vaginal region, and in regions of the body opened surgically) is brachytherapy, in which one or more radiation sources is brought, controlled by an afterloading device, in a precise and metered manner to the site of treatment in the body. The radiation source is then moved to provide a previously-calculated isodose contour. See, e.g., See, Nath, et al., 1995. Dosimetry of interstitial brachytherapy sources: Recommendations of the AAPM Radiation Therapy Committee Task Group No. 43, *Med. Phys.* 22: 209–234); Lukas, et al., Intraoperative Radiotherapy with High Dose Afterloading (Flabs Method), in: *Intraoperative Radiation Therapy"*, Proceedings 4th International Symposium IORT, Schildberg and Kramling, eds., 1992 (Verlag Die Blaue Eule, Essen).

In brachytherapy, there is a relatively short distance (i.e., typically 0.1–5 cm) between the radioactive source and the tissue which is to receive radiotherapy. It should be noted however that brachytherapy is a comprehensive term, and includes radiotherapy effected by interstitial, intercavitary, and surface application (plaque). Interstitial and intracavitary techniques are particularly advantageous where deep-seated lesions are involved while plaque therapy is particularly advantageous where superficial or accessible diseased tissue is involved. In contrast, another form of radiation therapy, "external beam therapy", involves treatment at relatively large distances (i.e., 50–500 cm) between the radiation source and the skin surface. Accordingly, with "external beam therapy," it generally is difficult to mitigate damage to underlying disease yet spare the normal tissues which may be included in the path of the radiation towards the target. Recent approaches using intensity-modulated radiotherapy (See, e.g. Tsai, et al., 2000. Dependence of linac output on the switch rate of an intensity-modulated tomotherapy collimator, *Med. Phys.* 27).

There are two general types of brachytherapy, those involving permanent implants and those which utilize temporary implants. Although a wide variety of radioactive elements ("radioisotopes") have been previously proposed for therapeutic use, only a relatively small number have actually been accepted and employed on a large-scale basis. This is due, at least in-part, to a relatively large number of constraining considerations where medical treatment is involved (i.e., the energy of the emitted radioactivity, half-life, availability, and the like). An element employed almost immediately after its discovery in 1898, was radium. Although radium possesses a long half-life (i.e., approximately 1600 years), a particularly undesirable property is the requirement for careful attention to the protection of medical personnel, as well as healthy tissue of the patient. This is due to its complex and highly penetrating gamma ray emission. To minimize exposure to medical personnel, specialized and sometimes complicated "after loading" techniques have been developed whereby the radioisotope is guided, for example through a hollow tube, to the treatment region following preliminary placement of the specialized appliances required.

More recently, permanent implants using radioactive "seeds" containing iodine-125 have been previously employed. Similarly, for temporary implants, cesium-137, iridium-192, and palladium-103 sources have been employed. These radionuclides will be briefly discussed, infra. In addition, the use of xenon-133 and xenon-131 have also be suggested.

In order to avoid harming the patient and to guarantee the requirements for accurate irradiation, the radioactive source(s) must be accurately positioned and fixed on or in the body. Only when this is ensured can programming of the required isodose contour take place and properly pre-planned irradiation be guaranteed. If the radiation source is not accurately positioned, there may be considerable over-dosage to normal (i.e., non-tumorogenic) tissue, with serious risk of harm to the patient, or exposure of medical staff to radiation. See, e.g., Gosh, 1991. Sicherheitstechnisch bedeutsame Ereignisse an Afterloadinganlagen: Untersuchungen zur Strahlenexposition, Folgerungen zur Sicherheit von Personal und Patient [Events with relevance to safety in afterloading systems: Investigations on radiation exposure, consequences for safety of staff and patient] *Diplomarbeit Berufsakademie, Karlsruhe*. Additionally, in cases of repeated radiation treatments, where a reduced radiation dose is given in each subsequent treatment, accurate localization of the radioactive source(s) at the site of treatment over a lengthy period is of particular importance.

II. Radionuclides Traditionally Utilized in Brachytherapy

Initially, interstitial implants were performed with radium-226 ($^{226}$Ra) needles. However, due to serious radiation safety considerations from the highly penetrating gamma-rays, this radioisotope has largely been replaced with other radionuclides. Currently, the vast majority of interstitial brachytherapy treatments in North America are done using either iridium-192 ($^{192}$Ir), iodine-125 ($^{125}$I), or cesium-137 ($^{137}$Cs) sources. Recently, palladium-103 ($^{103}$Pd) sources have also become available for permanent implants. A brief description of $^{192}$Ir, $^{125}$I, $^{137}$Cs, and $^{103}$Pd sources is given in the following sections.

1. Iridium-192 ($^{192}$Ir) Sources $^{192}$Ir is produced when stable $^{191}$Ir (37% abundance) absorbs a neutron. $^{192}$Ir decays with a short 73.83 day half-life to several excited states of $^{192}$Pt and $^{192}$Os which are both gamma ray emitters with a varying range of energies. The average energy of the emitted photons from an unencapsulated source is approximately 0.4 MeV. In the United States, $^{192}$Ir is used for interstitial radiotherapy is usually in the form of small cylindrical sources or "seeds" which are from 3 to 10 mm long and approximately 0.5 mm in diameter.

2. Iodine-125 ($^{125}$I) Sources $^{125}$I is produced when $^{124}$Xe absorbs a neutron, and then decays via electron capture. $^{125}$I itself decays with a half-life of only 59.4 days, by electron capture to the first excited state of $^{125}$Te, which subsequently undergoes internal conversion 93% of the time and otherwise emits a 35.5 keV gamma-ray. The electron capture and internal conversion processes give rise to characteristic x-rays. $^{125}$I for interstitial implants is available commercially in the form of small "seeds" of varying sizes and activities.

3. Palladium-103 ($^{103}$Pd) Sources $^{103}$Pd is formed when stable $^{102}$Pd absorbs a neutron. It decays via electron capture, mostly to the first and second excited states of $^{103}$Rh with a 17.0 day half-life. De-excitation is almost totally via internal conversion, leading to the production of characteristic x rays. Average photon energy is approximately 21 keV. $^{103}$Pd sources are similar in size and encapsulation to those for $^{125}$I sources, typically being 4.5 mm long and 0.8 mm in diameter.

4. Cesium-137 ($^{137}$Cs) Sources $^{137}$Cs possesses a half-life of 30 years. Gamma radiation from $^{137}$Cs has an energy of 662 keV, which in comparison to the other radionuclides in this section, is highly energetic.

III. Dose Formalisms in Brachytherapy (TG-43)

A large number of references have been published which introduce revised radiation sources, calibration standards, source strength specification quantities, and dose calculation formalisms for, e.g., $^{192}$Ir, $^{125}$I, and $^{103}$Pd sources. To promote accuracy and uniformity of clinical practice, the Radiation Therapy Committee of the American Association of Physicists in Medicine (AAPM) formed Task Group No. 43 (TG-43) to review publications on dosimetry of interstitial brachytherapy sources and recommend a dosimetry protocol which would include a formalism for dose calculations and a data set for the values of dosimetry parameters. See, Nath, et al., 1995. Dosimetry of interstitial brachytherapy sources: Recommendations of the AAPM Radiation Therapy Committee Task Group No. 43, *Med. Phys.* 22: 209–234). The TG-43 publication presented a formalism that clearly defined the necessary physical quantities (e.g., air kerma strength, radial dose function, anisotropy function, dose rate constant, and the like) for the calculation of accurate, quantitative dosimetric data.

Although the TG-43 protocol set forth dosimetric criteria for various interstitial brachytherapy sources, it failed to provide any dosimetric protocols for $^{252}$Cf, dealing instead only with $^{192}$Ir, $^{125}$I, and $^{103}$Pd radionuclides. Additionally, clinical data and experimental results have shown that specification of dose to muscle, rather than to water, is recommended for clinical dosimetry of $^{252}$Cf medical sources. This is in direct conflict with the recommendations of the TG-43 protocol since the kinetic energy released in matter (kerma) varies more between muscle and water for neutrons than for photons. Moreover, there are no reports which have: (i) formulated a $^{252}$Cf brachytherapy neutron dosimetry protocol which is similar to that set forth in the ICRU-45 protocol; (ii) quantitatively measured or calculated (using Monte Carlo methods) neutron or photon dose from various different $^{252}$Cf sources in a number of media using modern measurement techniques and apparatus or modern radiation transport codes with recent and accurate cross-section data; and (iii) compared these $^{252}$Cf dosimetry calculation to those previous reported. Accordingly, there remains an, as yet unfulfilled, need for an efficacious $^{252}$Cf brachytherapy dosimetry formalism which has utilized state-of-the-art methodologies in its derivation. Additionally, because $^{252}$Cf is the only feasible neutron-emitting radio-isotope, there exists the unique possibility to enhance $^{252}$Cf brachytherapy with neutron capture therapy (NCT) using various neutron capture agents with relatively high neutron capture cross-sections such as, for example, $^{10}$B, $^{157}$Gd, $^{3}$He, $^{133}$Xe, or $^{135}$Xe.

IV. Encapsulation and Delivery of Radionuclide Sources in Brachytherapy

As of August 2000, there are no medical institutions within the United States using $^{252}$Cf sources for tumor therapy. Neutron brachytherapy (i.e., insertion of the neutron-emitting source directly into or around the tumor) is markedly more effective than conventional photon radiotherapy in treating certain tumors, specifically bulky tumors and hypoxic (oxygen-deficient) tumors. For example, impressive results have been reported using $^{252}$Cf brachytherapy for advanced bulky gynecological tumors. See, Maruyama, et al. 1991. A review of californium-252 neutron brachytherapy for cervical cancer, *Cancer* 68: 1189, and also see, Maruyama, et al., 1985. Clinical trial of $^{252}$Cf neutron brachytherapy vs. conventional radiotherapy for advanced cervical cancer, *Int. J. Radiation Oncology, Biol. Phys.* 11: 1475. In addition, a recent workshop presented data on improved survivability for several types of bulky and recurrent tumors (e.g., head and neck, gynecological, rectal) from $^{252}$Cf brachytherapy followed by photon therapy, compared with photon therapy alone. See, Wierzbicki, 1996. Californium-Isotope for 21st century radiotherapy, NATO Advanced Research Workshop, Detroit, Mich., Apr. 24–28, 1996.

Generally, clinicians only have available a 25-year-old brachytherapy source design developed at Savannah River Laboratory (SRL) called the Applicator Tube (AT), which was designed similarly to the popularly utilized "radium needles" of that time period. See, e.g., Maruyama, et al., Californium-252 neutron brachytherapy, in: *Principles and Practices of Brachytherapy*, edited by S. Nag (Futura, Armonak, N.Y. 1997) pp. 649–687. These sources may be manually "loaded" into the patient and require treatment times of several hours. The currently available $^{252}$Cf AT source geometry has an active length of 15 mm and is double-encapsulated in an alloy comprising of 90% mass platinum and 10% mass iridium (Pt/Ir-10%) which is 23 mm long and 2.8 mm in diameter as now fabricated at Oak Ridge National Laboratory (ORNL) in Tennessee. A schematic diagram of an ORNL-fabricated $^{252}$Cf AT source geometry 10 is illustrated in FIG. 1. The geometry 10 includes a core wire 12, a primary capsule 14, a secondary capsule 16, a Bodkin eyelet 18, and two tungsten-arc weld closures 20, 22. Exemplary materials include a Pd-DF oxide composite for the core wire 12, Pt-10%Ir for the primary capsule 14, and Pt-10%Ir for the secondary capsule 16. Unfortunately, this AT-type source is rather large and cumbersome for use in restricted brachytherapy treatment geometries (e.g., the virulent brain tumor glioblastoma multiforme). Also, typical catheter outer diameters exceed 5 mm. Thus, there remains an, as yet, unfulfilled need for the development of a $^{252}$Cf source which possesses both high activity and overall small size.

SUMMARY OF THE INVENTION

The present invention discloses novel methodologies for use in the field of radiation oncology. More specifically, the present invention discloses brachytherapy dosimetric protocols, experimental measurements, and mathematical calculations utilizing the neutron-emitting radioisotope californium-252 ($^{252}$Cf).

In one embodiment of the present invention, the error associated with using a point source approximation for calculating the geometry factor for extended line sources was examined, prior to examining various brachytherapy dosimetric parameters using $^{252}$Cf as a neutron source, so as to maximize the efficacy and accuracy of those protocols employing $^{252}$Cf. It should be noted that, as expected, the two models (i.e., point source and line source) became comparable for large dimensionless (r/L) distances. Accordingly, a novel means of determining the geometry factor (also possibly referred to as the geometry function) using Monte Carlo methods was developed in which particle flux was tabulated in volume elements (3-D voxels similar to 2-D pixels or picture elements) where particles do not undergo physical interacts throughout the calculational model. In brief, for a total of three high dose rate (HDR) source types, differences between the line source approximation and the Monte Carlo-derived geometry factor were found to exceed 2% and occur at distances of approximately 0.5 to 0.8 mm. For these three HDR sources, a simple equation relating the radial distance to the diameter of the active source was developed to correlate differences in the geometry factor between the Monte Carlo calculations and line-source approximations. Geometry factor results calculated using Monte Carlo methods for three interstitial brachytherapy seeds demonstrated significant (>2%) differences from the single- and multi-point source approximations at distances of approximately 5.0 and 0.3 mm, respectively.

In a second embodiment of the present invention, a methodology for the characterization and determination of mixed-field dosimetry for $^{252}$Cf Applicator Tube (AT)-type medical sources, utilizing ionization chambers, GM counters, and Monte Carlo methods is disclosed. Unlike the previously utilized protocols for specifying brachytherapy dosimetry parameters such as TG-43, the present invention discloses administration of radiation dose to muscle, rather than radiation dose to water, for clinical dosimetry of neutron-emitting $^{252}$Cf medical sources. A dosimetry measurement protocol, similar to that set forth in utilized for the International Commission on Radiation Units and Measurements (ICRU) report number 45 (ICRU-45) protocol, with parameters determined specifically for $^{252}$Cf brachytherapy is disclosed. By comparison of experimental and calculative dosimetry results, correction factors were determined to compare and differentiate various dosimetry formalisms.

In a third embodiment, kerma relative to muscle was determined calcauatively for a variety of materials and compared with relative kermas for external neutron beams of three different energies by use of a Maxwellian model to characterize the $^{252}$Cf neutron energy spectrum.

In a fourth embodiment of the present invention, neutron isodose distributions and data necessary for clinical implementation of $^{252}$Cf sources are disclosed.

In a fifth embodiment, an encapsulation methodology for the sealed-source encapsulation of $^{252}$Cf is disclosed.

In a sixth embodiment, a container or "safe" for the storage of a $^{252}$Cf source is disclosed.

In a seventh embodiment, a methodology for the remote delivery (i.e., afterloading) of $^{252}$Cf brachytherapy sources is disclosed.

In an eighth embodiment, radiation dosimetry, characterization of the $^{252}$Cf thermal neutron fluence field, and techniques for clinical application of neutron capture therapy (NCT) enhanced $^{252}$Cf brachytherapy using NCT agents such as $^{10}$B, $^{157}$Gd, $^{3}$He, $^{133}$Xe, or $^{135}$Xe are disclosed.

BRIEF DESCRIPTION OF THE FIGURES

FIG. 3: illustrates an exemplar MCNP input file; wherein the source long-axis was oriented in the x-direction (e.g., axs 100, cx 0.017) while the tally cell sampling space was aligned with the z-axis (e.g., pz 0.02 . . . pz 0.51).

DETAILED DESCRIPTION OF THE INVENTION

Figure 1:
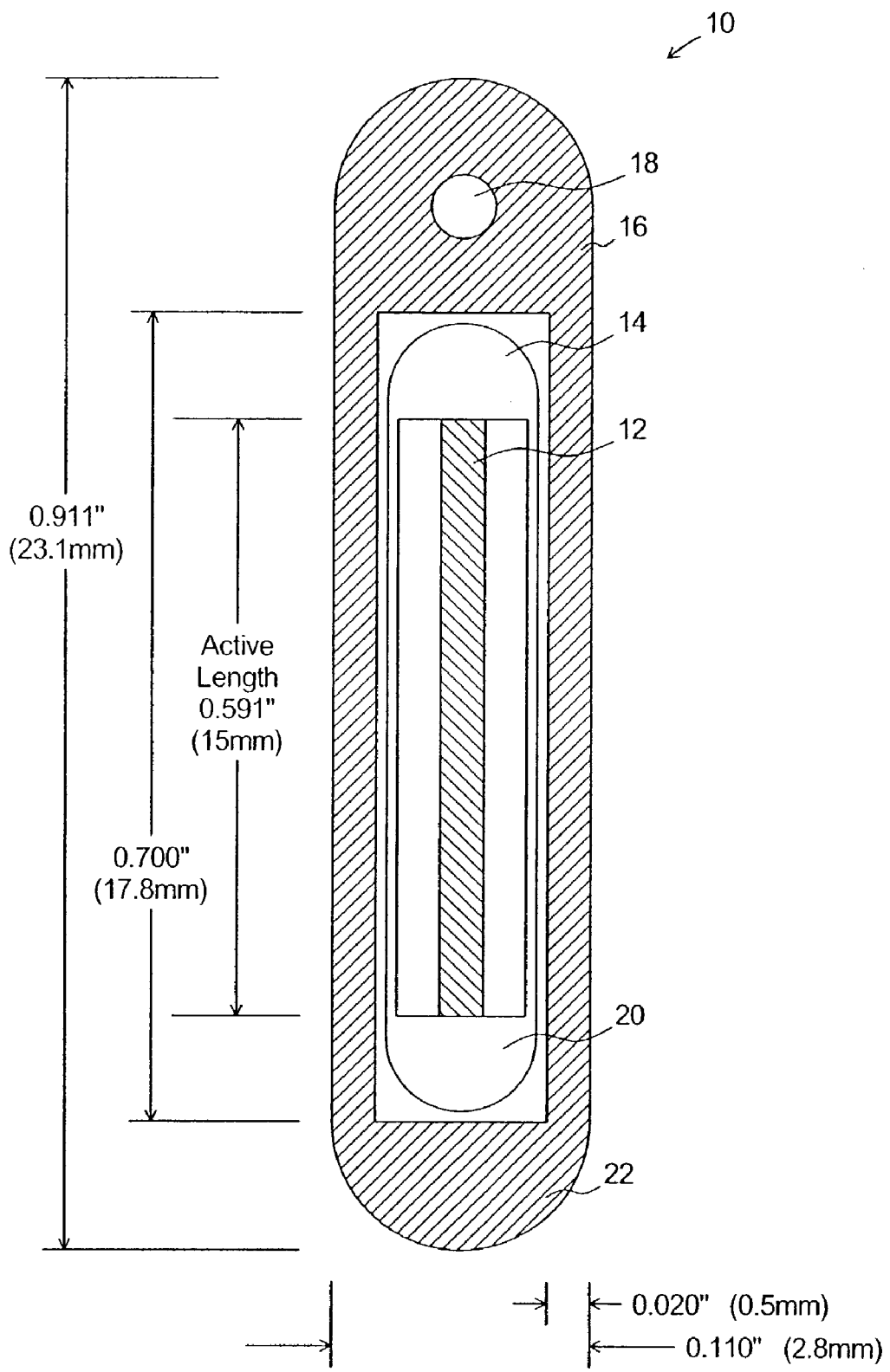
FIG. 1: a schematic illustration of an ORNL-fabricated $^{252}$Cf AT source geometry.

In brief, the present invention discloses the novel application of an International Commission on Radiation Units and Measurements (ICRU-45)-like dosimetry protocol (see, ICRU Clinical neutron dosimetry, Part I: determination of absorbed dose in a patient treated by external beams of fast neutrons, International Commission on Radiation Units and Measurements (ICRU-45, Bethesda, Md., 1989), to Californium-252 ($^{252}$Cf) neutron emitting brachytherapy sources, wherein numerous dosimetry protocol parameters were determined specifically for $^{252}$Cf. In addition, $^{252}$Cf neutron kerma, as determined using Monte Carlo computational methodologies, was analyzed for a variety of clinically-relevant tissues and dosimetry media. Measurements using both a miniature GM counter and two different types of TE chambers were used to determine the mixed-field (neutron and photon) dosimetry parameters for $^{252}$Cf AT sources. Comparisons were subsequently made between the results previously obtained by Colvett, et al. (1972. Dose distribution around a $^{252}$Cf needle, *Phys. Med. Biol.* 17: 356–364 and Rivard, et al. 2000. Calculated neutron air kerma strength conversion factors ($S_{kN}$) for a generically encapsulated Cf-252 brachytherapy source. *Nuclear Instruments and Methods in Physics Research A*; 2000.) and Krishnaswamy (1971. Calculation of the dose distribution about $^{252}$Cf needles in tissue, *Radiol.* 98: 155–160; 1972. Calculated depth dose tables for $^{252}$Cf sources in tissue, *Phys. Med. Biol.* 17: 56–63) by use of conversion factors derived to permit accurate quantitative comparisons.

The present invention also discloses methodologies for the sealed-source encapsulation of $^{252}$Cf, as well as for the remote delivery (i.e., remote afterloading) of $^{252}$Cf brachytherapy sources.

I. TG-43-Based Recommended Dose Formalisms

The dosimetry of sources used in interstitial brachytherapy has been the subject of considerable research in recent years. A large number of references have been published which introduce revised radiation sources, calibration standards, source strength specification quantities, and dose calculation formalisms. Additionally, some of these references have advocated revision of basic dosimetry data, including dose rate constants, radial dose functions, and anisotropy functions for, e.g., $^{192}$Ir, $^{125}$I, and $^{103}$Pd sources. With all of these reports appearing in the literature, the medical physics community is faced with a confusing situation regarding the quantitative selection of dosimetry data. In accord, the Radiation Therapy Committee of the American Association of Physicists in Medicine (AAPM) formed Task Group No. 43 (TG-43) and the AAPM Subcommittee on Low-Energy Interstitial Brachytherapy Dosimetry to review the recent publications on the dosimetry of interstitial brachytherapy sources and recommend a dosimetry protocol which would include a formalism for dose calculations and a data set for the values of dosimetry parameters. See, Nath, et al., 1995. Dosimetry of interstitial brachytherapy sources: Recommendations of the AAPM Radiation Therapy Committee Task Group No. 43, *Med. Phys.* 22: 209–234).

The TG-43 publication presented a formalism that clearly defined the necessary physical quantities (e.g., air kerma strength, radial dose function, anisotropy function, dose rate constant, geometry factor, and the like) for the calculation of accurate, quantitative dosimetric data. The work of TG-43 served a vital role in the field of radiation oncology because previous dose estimates were often only made on the basis of exposure calculated from activity. However, this proved to be problematic since the activity might be inferred by the manufacturer using one value of the constant and the dose might be calculated by the user from a different value. This is exemplified by the fact that the exposure rate constants, prior to 1978, for $^{192}$Ir, ranged from 3.9 to 5.0 R cm$^2$ mCi$^{-1}$ h$^{-1}$.

In part, because of such difficulties, the TG-43 recommendations included a new dose calculation formalism for the dosimetry of interstitial brachytherapy sources. Several new quantities were introduced, which differed conceptually from the quantities which were currently in use. For example, gamma ray constant, exposure rate constant, tissue attenuation factors, apparent activity, and exposure-to-dose conversion factors were not needed in the new formalism. Instead, only quantities directly derived from dose rates in water medium near the actual brachytherapy source were utilized. Some of these quantities included: dose rate constant, radial dose function, anisotropy function, anisotropy factor, and geometry factor. It should be noted that the TG-43-recommended values of dosimetry constants resulted in changes of up over 17% in the dosimetry of some interstitial brachytherapy sources.

The TG-43-recommended brachytherapy dosimetry protocol was based upon measured (or measurable) quantities and decouples a number of inter-related quantities. It also allows calculations of two-dimensional dose distributions (radial distance and polar angle) around brachytherapy sources. As previously noted, the dosimetry data endorsed by the report was found to result in absolute dose rate changes as large as 17%, relative to conventionally utilized treatment planning data. Generally, the dose calculation formalism proposed in the TG-43 report, in contrast to traditional methods using exposure rate constants and tissue attenuation factors, required input data consisting of dose rates from an actual source in a tissue equivalent phantom. Traditionally, the dose rate at a given distance from an interstitial brachytherapy source was calculated using a point-source approximation. In the protocol set forth by the TG-43, each of the quantities used to calculate absorbed dose rate was measured or calculated for the specific type of source in question and therefore depended upon source construction and geometry, in addition to the primary photon spectrum and medium. In contrast, much of the input data to the older, semi-analytical models, including exposure rate constants and buildup factors, were based upon the fundamental properties of the radionuclide.

One of the inherent problems with the older protocols is that they were based upon photon fluence around the source in free space, whereas clinical applications require dose distributions in a scattering medium such as a patient. Determination of two-dimensional dose distributions in a scattering medium from a knowledge of the two-dimensional distribution of photon fluence in free space is easily accomplished only for a mono-energetic, isotropic point-source. An actual brachytherapy source exhibits considerable anisotropy and for such sources it is unduly complicated to determine accurately dose distributions in a scattering medium from distributions of photon fluence in free space. The TG-43-recommended formalism solved this fundamental problem by a direct use of measured or measurable dose distributions produced by a source in water equivalent medium. In addition, the TG-43 protocol allows for two-dimensional dose calculations around cylindrically symmetric sources whereas the old protocol could handle one-dimensional, point isotropic sources only.

The following sections define several of the variables utilized by the TG-43 formalism.

1. Reference Point for Dose Calculations

The reference point $(r_0, \theta_0)$ is chosen in this report to lie on the transverse bisector of the source at a distance of 1 cm from its center (i e., $r_0=1$ cm and $\theta_0=\pi/2$). This choice of reference point for dose calculation in a medium is consistent with the traditional practice of using a distance of 1 cm from the source as a reference point.

2. Air Kerma Strength $[S_K]$

Air kerma strength is a measure of brachytherapy source strength, which is specified in terms of air kerma rate at the point along the transverse axis of the source in free space. It is defined as the product of air kerma rate at a calibration distance, d, in free space, K(d), measured along the transverse bisector of the source, and the square of the distance, d. The calibration distance d must be large enough that the source may be treated as a mathematical point. In actual practice, air kerma rate standardization measurements are performed in air and corrections for air attenuation are included. Whereas the measurements for source strength calibration may be performed at any large distance, d, it is customary to specify the air kerma strength in terms of a reference calibration distance, $d_0$, which is usually chosen to be 100 cm. It should be noted that the user typically does not perform the in-air calibration, which is primarily performed by the various standardization laboratories including: National Institute of Standards and Technology (NIST) and accredited dosimetry calibration laboratories (ADCLs) in the USA and the National Research Council (NRC) of Canada. However, it is the responsibility of the medical professional to verify the accuracy of source strength provided by the vendor. Typically, the treatment facility has a well-type ionization chamber that has a calibration traceable to the national standards for each type of brachytherapy source.

3. Dose Rate Constant [ˆ]

The dose rate constant is defined as the dose rate to water at a distance of 1 cm on the transverse axis of a unit air kerma strength source in a water phantom. It should be noted that ˆ is an absolute quantity, unlike several other variables in the TG-43 protocol which are normalized (relative) quantities. For specification of the dose rate constant, as well as relative dose distribution parameters, the TG-43 protocol generally recommended that liquid water be accepted as the reference medium. In determining the value of ˆ, the 1 cm distance is specified along the transverse axis of the actual source (rather than an idealized point source) relative to its geometric center. The constant includes the effects of source geometry, the spatial distribution of radioactivity within the source, encapsulation, and self-filtration within the source and scattering in the water surrounding the source. The numerical value of this quantity also depends on the standardization measurements to which the air kerma strength calibration of the source is traceable; in other words, if the air kerma strength standard for a given source is changed in the future, the value of ˆ will also be changed.

4. Geometry Factor $[G(r, \theta)]$

The geometry factor accounts for the variation of relative dose due only to the spatial distribution of activity within the source, ignoring radiation absorption and scattering in the source structure and surrounding medium (e.g. water or tissue).

5. Radial Dose Function $[g(r)]$

The radial dose function accounts for the effects of adsorption and scatter in the medium along the traverse axis of the source. The radial dose function applies only to the traverse axis (i.e., only for points with an angle of $\theta_0$, which is equal to $\pi/2$ or 90°). This function defines the fall-off of dose rate along the transverse axis due to adsorption and scattering in the medium. In addition, it can also be influenced by the filtration of radiation by the encapsulation and source materials. The radial dose rate function is similar to a normalized traverse-axis tissue-attenuation factor or absorbed dose to kerma in free space ratio. The geometry factor play a role in the calculation of the radial dose function in that it suppresses the influence of the inverse-square law on the dose distribution around the source.

6. Anisotropy Function $[F(r, \theta)]$

The anisotropy function accounts for the anisotropy of dose distribution around the source, including the effects of absorption and scatter in the medium. This two-dimensional function gives the angular variation of dose rate about the source at each distance due to self-filtration, oblique filtration of primary radiation through the encapsulation material, and radiation scattering in the medium. Due to large dose rate gradients encountered near interstitial sources, it is difficult to measure dose rates accurately at a distance of less than 5 mm from the source. In addition, the large dose rate variation arising from the inverse square law makes accurate interpolation of intermediate dose rate values difficult without an excessively large table of measured data. Thus, by suppressing inverse square law effects, extrapolation to small distances from dose rate profiles measured at distances of less than 10 mm from the source, as well as interpolation between sparsely distributed measured values, is usually more accurate.

7. Point Isotropic Source Approximation

Some clinical treatment planning systems for interstitial brachytherapy utilize the one-dimensional isotropic point-source model to compute interstitial source dose distributions. In this approximation, dose depends only on the radial distance from the source, the source strength, and radiation attenuation by the medium. If a large number of "seeds" are randomly oriented, or the degree of dose anisotropy around single sources is limited, the dose rate contribution to tissue from each "seed" can be well approximated by the average radial dose rate as estimated by integrating the single anisotropic "seed" source with respect to solid angle (steradians).

8. Anisotropy Factor [$\phi_{an}(r)$]

The anisotropy factor defines the ratio of the dose rate at distance r, averaged with respect to solid angle, to dose rate on the transverse axis at the same distance. For the sources considered within the TG-43 report, $\phi(r)$ is less than 1, having values ranging from 0.91 to 0.97 depending upon the specific source. However, $\phi(r)$ may exceed unity for positions close to the brachytherapy source or for large sources.

9. Anisotropy Constant [$\phi_{an}$]

The anisotropy factor $\phi_{an}$ may be approximated by a distance- and angle-independent constant, termed the anisotropy constant, which usually takes a value less than 1.00. It should be noted that the point source approximation gives a dose rate at a reference point in the medium on the transverse bisector at a distance of 1 cm from the source, equal to $\hat{\phi}_{an}(r)$ for a unit air kerma strength source. Thus, dose rate on the transverse axis in the medium is somewhat lower using the point-source approximation than the actual dose rate by approximately 3% to 9% for the sources considered within the TG-43 report.

II. Utilization of Californium-252 ($^{252}$Cf) in Brachytherapy

In 1950, the element californium (Cf) was first created at the Berkeley Crocker Laboratory in California through bombardment of helium nuclei onto a $^{242}$Cm target. See, Thompson, et al., 1950. The new element californium (atomic number 98), *Phys. Rev.* 80: 790–796. While this initial product was identified as $^{245}$Cf, the isotope $^{252}$Cf was not created until the MIKE thermonuclear test of 1952. Subsequently, microscopic amounts of $^{252}$Cf were first synthesized in 1958 at the Idaho National Engineering Laboratory through successive neutron captures by a $^{239}$Pu target. Still later, a large-scale effort was undertaken by the Savannah River Laboratory (SRL) in order to evaluate the market potential of $^{252}$Cf as a compact and long-lived source of neutrons. The first sale of milligram quantities of $^{252}$Cf occurred in 1971, and was utilized for activation analyses of specimens retrieved from the moon. The current cost of $^{252}$Cf is about $60/µg, and through generous loan agreements by the U.S. Department of Energy (DOE), various labs and university hospitals have been able to accurately determine the half-life, neutron and photon energy spectra, and various other properties of $^{252}$Cf. It should be noted that since 1973, most of the supply of $^{252}$Cf Supply for the Western world has been produced at Oak Ridge National Laboratory (ORNL) in the High Flux Isotope Reactor and recovered at the Radiochemical Engineering Development Center (REDC). See, Knauer and Martin, Californium-252 production and neutron source fabrication, in: *Californium252—Isotope for 21$^{st}$ Century Radiotherapy*, NATO Advanced Research Workshop, Detroit, Mich., April 24–28, 1996.

Due to its high yield of neutron emissions and relatively long half-life (2.645 years), $^{252}$Cf is the most useful neutron emitter out of all the approximately 6000 radionuclides now known. Although $^{260}$Md and $^{254}$Cf have been shown to have higher rates of spontaneous fission, and thus increased neutron yields, their half-lives of 32 and 60.5 days, respectively, are prohibitively short considering the sophisticated steps required for medical source fabrication. $^{252}$Cf mainly decays (96.9%) through alpha emissions to form $^{248}$Cm (concomitantly releasing He gas) and with only 3.1% of the $^{252}$Cf decaying via spontaneous fission. Through this later nuclear decay mechanism, 3.768 neutrons per fission event are released, for a total neutron yield of 2.314×10$^{12}$ neutrons/g/s. See, Knauer and Martin, Californium-252 production and neutron source fabrication, in: *Californium-252—Isotope for 21$^{st}$ Century Radiotherapy*, NATO Advanced Research Workshop, Detroit, Mich., Apr. 24–28, 1996. The $^{252}$Cf energy spectrum may be fit to a Watt fission model or a Maxwellian model with a most probable neutron energy of ~1 MeV As this energy spectrum is similar to that obtained from a nuclear reactor, $^{252}$Cf affords the opportunity for a compact and easily shieldable neutron source for use in both research and clinical medical applications.

$^{252}$Cf was initially suggested for clinical applications by Schlea and Stoddard in 1965. See, Schlea and Stoddard, 1965. Californium isotopes proposed for intracavitary and interstitial radiation therapy with neutrons. *Nature* 206: 1058–1059, 1965. and Maruyama, 1986. Californium-252: New isotope for human cancer therapy, *Endocurietherapy/Hyperthermia Oncol.* 2: 171–187. $^{52}$Cf is capable of providing a high degree of linear energy transfer (LET) and the neutrons emitted provide far greater efficacy in the treatment of tumors in oxygen-poor environments, as neutron are not dependent upon the formation of oxygen free radicals to elicit destruction of the tumor tissue. Furthermore, DNA damage is more likely mitigated through double-stranded DNA breaks rather than combinations of single-stranded breaks. In order to ascertain the feasibility of Schela and Stoddard's proposal, manually afterloaded sources were initially fabricated at SRL and were similar to the popularly utilized "radium needles" of that time period. Subsequently, AT sources have been used for over 25 years in the field of radiation therapy/oncology. See, e.g., Maruyama, et al., Californium-252 neutron brachytherapy, in: *Principles and Practices of Brachytherapy*, edited by S. Nag (Futura, Armonak, N.Y. 1997) pp. 649–687. The $^{252}$Cf AT source geometry has an active length of 15 mm, is double-encapsulated in Pt—Ir 10% mass tubes, is 23 mm long and 2.8 mm in diameter. A schematic diagram of an ORNL-fabricated $^{252}$Cf AT source geometry is illustrated in FIG. 1. As previously discussed, since only 3.1% of $^{252}$Cf decays produce neutrons (and almost 4 neutrons are generated by this decay event), and since the photons are primarily emitted by a multitude of spontaneous fission decay products, a departure from conventional measures of source strength (i.e., curies or becquerels) is made. By convention, throughout the world, $^{252}$Cf source strength is measured in mass (i.e., mg or µg) of $^{252}$Cf present. Though a Cf source is initially chemically pure, it typically contains up to 85% of $^{252}$Cf, with the remaining 15 atom percent being $^{249}$Cf, $^{250}$Cf, and $^{251}$Cf with $^{253}$Cf and $^{254}$Cf quickly decaying. These minor isotopes generally have a negligible dosimetric impact for most applications due to their long half-lives of 351, 13, and 898 years, respectively. See, Knauer and Martin, Californium-252 production and neutron source fabrication, in: *Californium-252—Isotope for 21$^{st}$ Century Radiotherapy*, NATO Advanced Research Workshop., Detroit, Mich., Apr. 24–28, 1996.

$^{252}$Cf emits both photons and neutrons of varied energy which interact with human tissue in various different manners. See, e.g., Schlea and Stoddard, 1965. Californium isotopes proposed for interstitial and intracavitary radiation therapy with neutrons, *Nature* 206: 1058–1059. Although neutron energies with energy of at least 20 MeV have been observed from $^{252}$Cf, the neutron energy spectrum falls off rapidly at both higher and lower energies for an unmoderated $^{252}$Cf source in air. These neutrons interact through elastic scattering with hydrogen nuclei, and are readily thermalized in vivo. As these neutrons reach equilibrium, they mainly either are captured by hydrogen (0.33 barns) in the $^1$H (n,γ=2.225 MeV) $^2$H reaction or interact with nitrogen (1.83 barns) in the $^{14}$N(n,p) $^{14}$C reaction. While the atom percent of nitrogen in human tissue is low when compared to that of hydrogen, the energy deposition from the proton causes high-linear energy transfer (LET) which has been shown to be more effective at cell killing than photons. See, Hall, Linear energy transfer and relative biological effectiveness, in: *Radiobiology for the Radiobiologist* (Lippincott, Philadelphia, Pa., 1994) pp. 153–164. The prompt photons from alpha decay and $^{248}$Cm relaxation are of high energy, and react via pair production and the Compton effect. Other photons emitted through spontaneous fission products are generally of much lower energy, are attenuated to a greater extent by the Pt/Ir-10% encapsulation, and react via the photoelectric and Compton scattering. Roughly one-third of the radiation dose (gray) at 1 cm is due to photon emissions, and their effect is smaller when the relative biological effectiveness (RBE) of the neutrons is considered. Though RBE is a function of many factors, a value of 6 for low dose rate (LDR) irradiation with $^{252}$Cf neutrons has been adopted for various tumor sites. See, e.g., Maruyama, et al., 1991. Clinical study of relative biological effectiveness for cervical carcinoma treated with californium-252 neutrons, *Br. J. Radiology* 63: 270–277.

A mathematical model using the product of the physical dose multiplied by the relative biological effectiveness (RBE) for that specific dose rate and anatomical site for both healthy and malignant tissues will be incorporated into the source specification (e.g., g(r) and Λ), since radiation from $^{192}$Ir and of $^{252}$Cf have markedly different biological responses and since a biological dose rate factor is not common in commercial treatment planning systems. For $^{252}$Cf, the majority of physical dose, and large majority of biological effective dose is deposited by neutrons. Therefore, use of conventional clinical applicators (e.g., Fletcher-Suit for gynecological sites) with $^{252}$Cf is contra-indicated since the shielding material (e.g., tungsten or lead used to protect the bladder and rectum) is relatively ineffective for neutrons as compared with photons.

Although numerous, recent articles have been published which discuss dosimetric protocols for the use of various radionuclides in brachytherapy, these have failed to provide quantitative dosimetric data for the use of $^{252}$Cf. For example, as previously discussed, TG-43 protocol has set forth dosimetric criteria for various interstitial brachytherapy sources. See, Nath, et al., 1995. Dosimetry of interstitial brachytherapy sources: Recommendations of the AAPM Radiation Therapy Committee Task Group No. 43, *Med. Phys.* 22: 209–234. However, the TG-43 formalism fails to provide to provide any dosimetric protocols for $^{252}$Cf, dealing instead only with iridium-192 ($^{192}$Ir), iodine-125 ($^{125}$I), and palladium-103 ($^{103}$Pd) radionuclides. Additionally, it has been shown that specification of dose to muscle, rather than to water, is recommended for clinical dosimetry of $^{252}$Cf medical sources. This is in direct conflict with the recommendations of the TG-43 protocol. Moreover, there are no reports which have: (i) formulated a $^{252}$Cf brachytherapy neutron dosimetry protocol which is similar to that set forth in the ICRU-45 protocol; (ii) quantitatively measured the neutron dose from various different $^{252}$Cf sources in a number of media using modern measurement techniques and apparatus; (iii) utilized Monte Carlo calculated $^{252}$Cf-neutron dosimetry according to TG-43 recommendations; and (iv) compared these novel $^{252}$Cf dosimetry results to those previous reported.

III. Principles of Dosimetry in Neutron Fields

The fields produced by neutron-emitting radionuclides, such as $^{252}$Cf, are always accompanied by gamma rays (-rays) originating from the neutron-emitting target, from the primary shielding and field-limiting system, and from the biological object or phantom being irradiated. Because of the differences in relative biological effectiveness of these two radiation components (which may depend upon the specific biological end-point), it is necessary to determine separately the neutron absorbed dose in tissue ($D_n$) as well as the -ray absorbed dose in tissue (D). In order to compare the biological and clinical effects of neutron beams of different energies, it is important to obtain information about the radiation quality which can be related to neutron energy spectra or microdosimetric spectra. See, e.g., ICRU Clinical neutron dosimetry, Part I: determination of absorbed dose in a patient treated by external beams of fast neutrons, International Commission on Radiation Units and Measurements (ICRU 45, Bethesda, Md., 1989).

An evaluation of the separate absorbed dose components can be made with a single instrument such as a proportional counter. This method requires the unfolding of the energy deposition events caused by protons and heavy ions from those caused by electrons. See, e.g., August, et al., 1978. Gamma measurements with a non-hydrogenous Rossi Counter in a mixed field, in: *Proceedings of the Sixth Symposium on Microdosimetry*, EUR 6064 (Harwood) pp. 441–446. Generally, however, two instruments with different relative neutron sensitivities are used for the evaluation of the component radiation. One of these, e.g., a tissue-equivalent (TE) ionization chamber or calorimeter, will have approximately the same sensitivity to neutrons and photons, whereas the second instrument is chosen for its reduced neutron sensitivity relative to that for photons.

A. Dosimetric Methods

The use of calibrated A-150 plastic TE ionization chambers with TE gas (methane- or propane-based) has typically been recommended as the practical method of obtaining the tissue kerma in air and the absorbed dose in a TE phantom. This recommendation is based on the fact that TE chambers have been used as the principal dose measuring instrument by the neutron therapy groups in Europe, United States, and Japan. The American groups all use a common set of TE ionization chambers, which generally employ a 1.0 cm$^3$ spherical chamber as the principal instrument for measurements of neutron tissue kerma in air and absorbed dose in a phantom, and a 0.1 cm$^3$ cylindrical chamber for spatial dose distribution measurements in a TE liquid phantom. Previously, in Europe, the various institutes developed and constructed their own dosimeters; these, unavoidably, show mutually different characteristics. Thus, it was subsequently decided that all European groups should also use a common type of ionization chamber to check their other dosimeters. See, Broerse and Mijnheer, 1981. *Basic Physical Data for Neutron Dosimetry*, EUR 5629, pp. 311–319.

By convention, the TE ionization chambers should have applied to them a calibration factor for $^{60}$Co, $^{137}$Cs, or 4 MV X rays and this calibration should be directly traceable to a national standards laboratory. The ionization chamber method can be compared with other measurement systems, and in particular those that do not require calibration in a known radiation field are useful. A dosimeter which can be used for this purpose is the TE calorimeter. See, e.g., ICRU Clinical neutron dosimetry, Part I: determination of absorbed dose in a patient treated by external beams of fast neutrons, International Commission on Radiation Units and Measurements (ICRU 45, Bethesda, Md., 1989). An alternative method for the determination of neutron kerma is to measure fluence and apply a fluence to kerma conversion factor. Activation detectors and fission counters (See, e.g., Porter. et al., 1975. A novel fast neutron dosimeter based on fission chambers, *Phy. Med. Biol.* 20: 431) may be utilized for this purpose.

1. Materials Used in the Construction of Ionization Chambers

A common electrically conductive plastic used in the construction of TE ionization chambers has been a particular muscle-equivalent formulation designated A-150. A-150 plastic is generally supplied as small chips or granules suitable for use in molding, or in various sizes of stock and custom-molded shapes for more direct use. It consists of a homogeneous mixture of polyethylene, nylon (DuPont ZYTEL 69®), carbon, and calcium fluoride. See, e.g., Smathers, et al., 1977. Composition of A-150 tissue-equivalent plastic, *Med. Phys* 4: 74. Based upon extensive experimental and computational analysis of the end-product (See, e.g., Goodman, 1978. Density and composition uniformity of A-150 tissue-equivalent plastic, *Phys. Med. Bio.* 23: 792; Smathers, et al., 1977. Composition of A-150 tissue-equivalent plastic, *Med. Phys.* 4: 74) researchers have arrived at the elemental weight composition for A-150 plastic. Ideally, each new batch of mixture which is intended for fabrication of instrument components for which the elemental composition is critical is analyzed thoroughly, either at its source or by the end-user. In particular, it should be noted that the accuracy of the measured neutron dose is very strongly dependent on the exact hydrogen content of the material.

A-150 TE plastic is not identical in elemental composition to ICRU muscle tissue due to the large admixture of carbon required for electrical conductivity and lack of oxygen providing structural stability. Deviations from muscle equivalence will thus necessarily be reflected in a kerma-factor ratio for the two media which is different from unity. The density of molded A-150 plastic is 1.127±0.005 g/cm$^3$, and does not appear to depend upon the specific molding technique (See, e.g., Goodman, 1978. Density and composition uniformity of A-150 tissue-equivalent plastic, *Phys. Med. Biol.* 23: 792).

Tissue-equivalent gas is recommended for use in homogeneous TE ionization chambers for measuring the total absorbed dose. The composition of the gas should be verified by analysis since impurities in the gas may have a significant effect on the chamber response.

B. Physical Parameters

Variation in the results obtained in neutron dosimetry inter-comparisons can, in part, be traced to differences in the basic physical parameters which have been used to convert specific dosimeter reading to tissue kerma in free air or to absorbed dose in a phantom. See, e.g., ICRU Clinical neutron dosimetry, Part I: determination of absorbed dose in a patient treated by external beams of fast neutrons, International Commission on Radiation Units and Measurements (ICRU 45, Bethesda, Md., 1989). These parameters include, but are not limited to: (i) the average energy required to create an ion pair in the gas; (ii) the gas-to-wall absorbed-dose conversion factor; (iii) the neutron kerma ratio; (iv) the displacement factor; and (v) the relative neutron sensitivity of dosimeters used for photon-fraction determinations.

In order to achieve consistency in neutron dosimetry, it is necessary to use a set of these basic parameters which is appropriate for a given neutron spectrum and which is obtained from a common source. Neutron spectral measurements are the necessary source input for computation of these basic physical parameters. These measurements have been accomplished by many methods (e.g., proton recoil counters, time-of-flight, and foil activation). The techniques are those developed over a period of years for use in reactor and neutron physics research. However, for neutrons with energy above 20 MeV, uncertainties in the cross-section information tend to increase the uncertainty in the data with increasing energy.

Some types of detectors (e.g., Geiger-Muller counters) have a sensitivity which varies with photon energy. In order to determine the relative photon sensitivity of these dosimeters, an approximate knowledge of the photon spectrum in the neutron field is necessary. When no information is available, these values are taken equal to unity. This assumption may, however, introduce an uncertainty of several percent in the determination of the photon absorbed dose in a neutron beam.

Several physical parameters utilized in the conversion of specific dosimeter readings to tissue kerma in free-air or to absorbed dose in a phantom will be defined, infra.

1. Energy Required to Create an Ion Pair

The parameter which is used to convert the charge produced within the chamber to energy deposited in the gas (W), is defined as the mean energy required to form an ion pair in the chamber gas or gas mixture. The magnitude of this parameter depends upon the type and spectra of the secondary charged particles, and on the chemical composition of the gas.

In both United States and European institutions which are engaged in neutron therapy, the values of $W_c/W_n$ used for TE gas have been set forth in several publication, especially ICRU (Clinical neutron dosimetry, Part I: determination of absorbed dose in a patient treated by external beams of fast neutrons, International Commission on Radiation Units and Measurements (ICRU 45, Bethesda, Md., 1989), which recommended a value of 0.95.

2. Gas-to-Wall Absorbed Dose Conversion Factor

In brief, the gas-to-wall dose conversion factors for neutrons is made difficult due to several basic problems: (a) adequate measurements of stopping power for the charged particles generated by fast neutrons in various materials; (b) the equilibrium charged-particle spectrum created by the neutrons has not been completely characterized; and (c) the range of the low-energy heavy recoils is limited. The latter factor results in particles existing in the various categories of "starters", "stoppers", "insiders", and "crossers" relative to the chamber cavity and the dose conversion factor is therefore a function of cavity size and neutron energy.

3. Neutron Kerma Ratio

The relevant quantity for medical and biological applications of fast neutrons is the absorbed dose in tissue of specific composition (e.g., soft tissue as defined by ICRU) for muscle. The differences in the oxygen and carbon content of TE plastic and muscle tissue and differences in the oxygen and carbon neutron cross-sections results in a muscle/TE plastic (A-150) kerma ratio which deviates from unity. A ratio in the range 0.93–0.97 has generally been accepted for the neutron therapy beams presently used for treating patients. The uncertainty associated with the ratio increases with neutron energy, due to a lack of cross-section information in the higher energy range. See, e.g., ICRU Clinical neutron dosimetry, Part I: determination of absorbed dose in a patient treated by external beams of fast neutrons, International Commission on Radiation Units and Measurements (ICRU 45, Bethesda, Md., 1989).

ICRU provided a markedly more accurate methodology for the calculation of kerma ratios, which had previously been obtained from the tables of kerma per unit neutron fluence. See, e.g., Caswell, et al. 1980. Kerma factors for neutron with energies below 30 MeV, *Rad. Res.* 83: 217. Generally, kerma calculations have been demonstrated to be spectrum dependent, and information concerning the radiation spectrum at the reference point so be ascertained in these calculations, although changes in neutron spectrum as the beam passes into a phantom or patient are though not to appreciably affect the kerma ratio.

4. Displacement Correction Factor

For absorbed dose specification as a function of depth and/or position in a large tissue-equivalent phantom, the analysis of dosimetric measurements using ionization chambers must account for the displacement of the phantom material brought about by the introduction of the dosimeter. A displacement correction is to be applied to the measured ionization charge (dose) to compensate for the differences in attenuation and scattering of the primary radiation caused by the displacement of the phantom material by the ion chamber, thus obtaining the charge (dose) which would have been measured by a hypothetical ion chamber of zero volume centered at the same location, for which the displacement correction factor would be unity.

This correction can be taken into account by using a multiplicative correction factor. Alternately, another approach is to account for the displacement by stating the effective measuring point as a certain fraction of the radius of the gas cavity of the ionization chamber in front of the geometrical center. The application of a multiplicative displacement correction factor is preferable at the reference point. Generally, in the United States two values for multiplicative displacement correction factors for their two common ionization chambers are utilized. It should also be noted that uncertainties in the displacement correction factor (e.g., dependence on neutron energy) are indicative of the importance of using small ionization chambers.

5. Relative Neutron Sensitivity

Assessment of the photon component of absorbed dose in a neutron beam is made using a dosimeter which is relatively insensitive to neutrons. The accuracy to which neutron absorbed dose can be calculated is greatest when a dosimeter with the smallest possible neutron sensitivity relative to its photon sensitivity is used. See, e g, ICRU Clinical neutron dosimetry, Part I: determination of absorbed dose in a patient treated by external beams of fast neutrons, International Commission on Radiation Units and Measurements (ICRU 45, Bethesda, Md., 1989). A dosimeter which has a particularly low relative neutron sensitivity value is a small Geiger-Muller (GM) counter used with an energy compensating filter. GM tubes, with their energy compensating filters, have a high thermal-neutron sensitivity and should be shielded by a thermal-neutron absorber which does not emit prompt y radiation in the neutron capture process. A commonly chosen material is lithium ($^6$Li) in the form of the metal or compressed lithium fluoride ($^6$LiF) powder. It should be noted that these detectors typically have a dead-time of approximately 30 µs which may become significant at photon absorbed dose rates in excess of about 2 mGy min$^{-1}$. Additionally, dead-time may also be problematic with respect to high-intensity pulsed beams. If it is not possible to reduce the output of the neutron source sufficiently, the use of another type of dosimeter is required.

The most commonly used alternative dosimeter and that which is preferred by many of the US neutron therapy groups is the non-hydrogenous ionization chamber. Several wall and gas combinations have been used, in particular C—$CO_2$ and Mg—Ar. However, it should be noted that utilization of the former chamber is not recommended due to its: higher relative neutron sensitivity value, different saturation characteristics to neutrons and photons, and showing shows anomalous characteristics due to gas leakage through the graphite walls. It should be recognized that measurements of relative neutron sensitivity which are made in air cannot be applied to determine the photon dose component in phantom unless the walls of the chamber are thick enough to stop the most energetic recoil protons generated within the phantom. In addition, relative neutron sensitivity varies with cavity size, so that any measured data are only valid for the specific geometry of the chamber being utilized.

C. Determination of Absorbed Dose

In principle, relative absorbed dose distributions for neutron beams are determined in a similar way as for photon beams. However, the primary difference compared with the procedure applied for photon beams is that in neutron dosimetry the separate neutron and photon absorbed doses must be determined. This implies that at any point the readings of two detectors have to be evaluated in order to obtain the neutron absorbed dose in tissue ($D_N$) and the γ-ray absorbed dose in tissue ($D_G$) at that point. These values should be related to the absorbed dose values at the given reference point. It is generally assumed that the physical parameters applied to calculate $D_N$ and $D_G$ from the detector readings are independent of the position of the detector within the beam.

1. Central-Axis Absorbed-Dose Distribution

When measuring central-axis depth-dose curves by means of ionization chambers a displacement correction has to be made. A multiplicative displacement correction factor cannot be used at depths close to the dose maximum. It is therefore recommended that a radial displacement be used The increase in absorbed dose at depths less than the build-up depth should be assessed by means of thin-walled ionization chambers by adding layers of, for example, A-150 plastic.

2. Isodose Distributions

Central-axis absorbed-dose distributions are usually combined with transverse measurements at several depths to obtain isodose distributions. In principle, the same methods for neutron beams as for photon beams may be employed, due to the great similarity in isodose curves. However, separate isodose curves for neutrons, as well as for photons, must be generated in the neutron beams. The stage at which these separate does components are combined is dependent upon the specific dose specification procedure. ICRU 45 describes the influence of shielding and collimators on the separate neutron and γ-ray absorbed-dose beam profiles.

3. Absorbed-Dose Specification

Because of their significantly different biological effectiveness, the separate neutron and γ-ray dose components (i.e., $D_N$ and $D_G$, respectively) should be determined as accurately as possible at all relevant positions, for different field sizes and irradiation conditions. There are two aspects of dose specification, namely the prescription of absorbed dose given for daily radiotherapy treatments and the reporting of the absorbed doses at the conclusion of a patient's treatment. It is not practical, however, to use two figures for the daily dose prescription, thus a single parameter is utilized. Three alternatives are possible. First, total absorbed dose ($D_N+D_G$), which is the system adopted within the United States, as this quantity can be assessed with the lowest overall uncertainty and the distribution can be measured with a single instrument. Second, the neutron absorbed dose ($D_N$) can be used. Third, total dose equivalent ($D_{Eq}=\tau D_N+D_G$) has been introduced where $\tau$ is a relative biological effectiveness (RBE) weighting factor indicating the effectiveness of the neutron component compared with the γ-ray component for relevant effects on tumors and normal tissues.

For the reporting of absorbed dose at the end of treatment it is necessary that both components are ascertained. ICRU has made recommendations for the final reporting of external beam therapy with photons and electrons and where applicable these recommendations should be followed for external neutron beam therapy. In the ICRU reports, the position has been defined at which the target absorbed dose should be specified. This definition should be followed for neutron dosimetry and at that position both components should be given. There are different ways in which these numbers can be quoted and it is recommended to give total absorbed dose with the γ-ray absorbed dose in brackets. In some European centers it is common clinical practice to specify the absorbed dose at a certain "total effective-dose" isodose curve which surrounds the target area, although it should be noted that the relative γ-ray contribution may vary over such a "total effective-dose" isodose curve.

4. Description of Irradiation Technique

The ICRU protocol has stated that the specification of target absorbed dose, alone, is not sufficient for reporting. Instead, it is recommended that information on the irradiation technique be given to facilitate the comparison of biological and clinical results obtained with different neutron sources. The ICRU recommends that the following information relevant to the irradiation conditions be specified.

Radiation Quality: The principal factors affecting the neutron spectrum incident on a phantom should be specified. These are: the incident charged-particle type and energy, target material and target thickness, and the thickness and material of the filter in the primary neutron beam.

Geometrical Conditions: Information on the geometrical conditions of irradiation should be provided (e.g., the number and arrangements of the beams, source to surface distance, patient positioning, and the like).

Field Size: The field size, which is determined by the combination of various pertinent parameters, including, but not limited to: neutron energy, collimator size, field shaping devices, distance, and the like, can be significantly expressed only in terms of the dose distributions achieved in a tissue-equivalent phantom. The geometrical field size usually corresponds to the dimensions of the plane figure described by the intersection of the 50% isodose surface and the plane that passes through, and is normal to, the central axis at the location of the relative dose maximum. Agreement between the size and position of the neutron beam and optical mechanical beam-localizing devices should be established (e.g., by means of radiographic film). Additionally, where relevant, the absorbed dose to shielded sites should also be specified. Field size is not a parameter related to brachytherapy.

Beam Modifying Devices: Information on wedges, filters and shielding blocks should be given. Also, the effect of such modification on field uniformity should be determined.

Time-Dose Patterns: It is recommended that, at a minimum, the number of fractions and the overall treatment time (in days), should be provided. If NSD calculations are made for neutron treatments, it should be stated what exponents for N and T were utilized. It should also be clear if the NSD formula has been applied to the neutron absorbed dose, the total absorbed dose, or the "total effective dose". Information on the target absorbed dose rate may also be useful.

IV. Refinements to the Dosimetry Factor Used in the AAPM Task Group Report No. 43 Necessary for Brachytherapy Dosimetry Calculations Using $^{252}$Cf According to the Radiation Therapy Committee of the American Association of Physicists in Medicine (AAPM) Task Group No. 43 brachytherapy dosimetry protocol (TG-43), a geometry factor may be used to account for the relative dose rate distribution due only to the spatial distribution of radioactivity for the source in question. See, Nath, et al., 1995. Dosimetry of interstitial brachytherapy sources: Recommendations of the AAPM Radiation Therapy Committee Task Group No. 43, *Med. Phys.* 22: 209–234). In TG-43, two types of spatial distributions are examined: point and line source. In the present invention, the equivalence and errors associated with use of a point source approximation for an extended line source were examined. The utility of this approach is to determine when it is appropriate to use either approximation, and to determine locations in the vicinity of a radioactive source in which there is no mathematical error when using the point source approximation.

Prior to examining various brachytherapy dosimetric parameters using $^{252}$Cf as a neutron source, the errors associated with using a point source approximation for calculating the geometry factor for extended line sources was examined so as to maximize the efficacy and accuracy of those protocols employing $^{252}$Cf, as will be present infra. It should be noted that, as expected, the two models became comparable for large dimensionless (r/L) distances. Accordingly, a novel means of determining the geometry factor using Monte Carlo methods was developed in which particle flux was tabulated in voxels where particles do not undergo physical interacts throughout the calculational model. In brief, for a total of three HDR source types, differences of at least 2% between the line source approximation and the Monte Carlo-derived geometry factor were found to occur at distances less than 0.8 mm. For these three HDR sources, a simple equation relating the radial distance to the diameter of the active source was developed to correlate differences in the geometry factor between the Monte Carlo calculations and line source approximations. Geometry factor results calculated using Monte Carlo methods for three interstitial brachytherapy seeds demonstrated significant (>2%) differences from the single- and multi-point source approximations at distances of approximately 5 and 0.3 mm, respectively.

A. Mathematical Methodologies

At distances close to a source where the active source diameter may not be considered negligible, the line source approximation may yield significant errors in evaluation of the geometry factor where significant is defined by AAPM TG-56 as ±2% for brachytherapy sources. For some clinical sources, the line source model is inapplicable due to the spatial distribution of radioactivity within the source. An example are "seeds" which contain spherical ion exchange resin beads in which the radioactivity is not distributed in a linear manner. See, e.g., Wallace and Fan, 1998. Evaluation of new brachytherapy iodine-125 source by AAPM TG-43 formalism, *Med. Phys.* 25: 2190–2196; (1998); Wierzbicki, et al., 1998. Calculated dosimetric parameters of the IoGold $^{125}$I source Model 3631-A, *Med. Phys.* 25: 2197–2199;

Wallace and Fan, 1999. Report on the dosimetry of a new design $^{125}$I brachytherapy source: Evaluation of MED3631-A/M $^{125}$I sources by AAPM TG-43 formalism, *Med. Phys.* (in press, September 1999). The geometry factor may be refined through its rigorous calculation using Monte Carlo methods instead of point or line source approximations. For these calculations, description of the spatial distribution of radioactivity within the source is necessary. However, details regarding the source encapsulation thickness or composition are not necessary as radiation transport is not performed. While one might approximate the radioactive elements within each of these sources as point sources to derive the geometry factor, this method may fail at distances near the source. In practice, use of this method may provide more accurate results than using point or line source approximations when determining brachytherapy dosimetry parameters. This is because both the point or line source approximations determine the geometry factor at a point location while the Monte Carlo methodology presented herein calculates the geometry factor over the volume in which dosimetry parameters, such as absorbed dose or photon energy spectra for convolution with collisional kerma coefficients, are integrated.

While it is trivial to determine the geometry factor using the point source approximation, the general form of the line source approximation may be determined from Equations 1–4, infra.

Geometry Factor General Form:

$$G(r,\theta) = \frac{\beta}{(Lr\sin\theta)} \quad (1)$$

Geometry Factor Along the Source Axis:

$$G(r,\theta = 0^0) = \frac{1}{\left[r^2 - \left(\frac{L}{2}\right)^2\right]} \quad (2)$$

Geometry Factor Along the Source Transverse Plane:

$$G(r,\theta_0) = \frac{2\arctan\left(\frac{L}{2r}\right)}{[Lr]} \quad (3)$$

Geometry Factor Explicit Form:

$$G(r,\theta) = \frac{\arctan\left[\frac{L}{2r\sin\theta} + \cot\theta\right] + \arctan\left[\frac{L}{2r\sin\theta} - \cot\theta\right]}{Lr\sin\theta} \quad (4)$$

Where:
r=the radial distance from source center to point of interest [cm]
β=angle subtended by the active source length at point (r,θ) [radians]
θ=angle from source long axis to point of interest [radians]
L=source active length [cm]
G(r, θ)=geometry factor [cm$^{-2}$]
G(r$_o$, θ$_o$)=geometry factor at r$_0$=1 cm, and θ$_o$=90° [cm$^{-2}$]

The angles, θ, in which the line source approximation (see, Equation 4) is equal to the point source approximation; this is defined as the 100% equivalence curve and later shown in FIG. 2. These data, as a function of radial distance, are presented as a dimensionless distance, r/L. As it has been recommended that the accuracy of dose calculations for brachytherapy implants be at least ±2% (see, Nath, et al. 1995. Dosimetry of interstitial brachytherapy sources: Recommendations of the AAPM Radiation Therapy Committee Task Group No. 43, *Med. Phys.* 22: 209–234), it is of interest to determine the errors in the geometry factor associated with using the point source approximation for extended sources at a variety of locations.

1. Monte Carlo Method for Derivation of the Geometry Factor

In comparison to the line or point source approximations, the geometry factor may be derived using an alternative and more rigorous methodology with probabilistic Monte Carlo methods commonly used for calculating brachytherapy dosimetry parameters. Here, the mass density of all materials (e.g., phantom, capsule, source, and the like) is made zero such that particles of arbitrary energy stream from their point of origin as there are no physical interactions. While these parameters would need to be determined for dosimetry calculations, for example with the MCNP*F8 tally using coupled photon and electron transport, there would be no need to redefine the volume elements (voxels) as those established for geometry factor calculations would be suitable. Particle flux is calculated within voxels positioned at locations relative to the source throughout the phantom. This method of calculating the geometry factor may be used for sources with any spatial distribution of radioactivity. While this methodology may have varying degrees of error due to use of voxels with finite volumes, these errors become negligible through implementation of relatively small voxels. See, Anderson, 1973. Status of dosimetry for $^{252}$Cf medical neutron sources, *Phys. Med. Biol.* 18: 779–799. Furthermore, these calculations may be performed in a quick manner using the MCNP program (see, Briesmeister, 1997. MCNP—A General Monte Carlo N-Particle Transport Code System, Version 4B (MCNP4B, Los Alamos National Laboratory, LA-12625-M), with calculations distributed on multiple machines (see, Geist, et al., PVM: Parallel Virtual Machine—A User's Guide and Tutorial for Networked Parallel Computing (The MIT Press, Cambridge, Mass., 1994); Rivard, 1999. Dosimetry for $^{252}$Cf neutron emitting brachytherapy sources: protocol, measurements, and calculations, *Med. Phys.* 26: 1503–1513). Though the Monte Carlo method as used by MCNP was hastened through the use of a parallel virtual machine (PVM), this method was not specific to MCNP and could have been performed using other programs which employ Monte Carlo techniques.

For calculating the geometry factor using Monte Carlo methods, the F4 voxel flux tally machines (see, Geist, et al. PVM: Parallel Virtual Machine—A User's Guide and Tutorial for Networked Parallel Computing (The MIT Press, Cambridge, Mass., 1994) within MCNP was employed and photons per cm$^2$ per starting particle within each voxel. Using this approach, by way of example and not of limitation, the geometry factor was determined for six brachytherapy sources. These sources included: (i) $^{192}$Ir high dose rate (HDR) sources by Nucletron Corporation (μSelectron part No. 080950 with a length of 3.5 mm and diameter of 0.60 mm, the newer μSelectron part No. 105.002 with a length of 3.6 mm and diameter of 0.65 mm) and a Varian Associates (VariSource, 10 mm in length and 0.34 mm in diameter) (see, Meigooni, et al., 1997. Dosimetric characteristics of a new high-intensity $^{192}$Ir source for remote after-loading, *Med. Phys.* 24: 2008–2013); (ii) [103]Pd interstitial seed by North American Scientific (MED3633, 4 resin beads 0.50 mm in diameter and coated with [103]Pd and spaced 1.50, 0.90, −0.90, and −1.50 mm on center from the transverse plane); and (iii) two $^{125}$I seeds also by North American Scientific (MED3631-A/S and MED3631-A/M). It should be noted, however, that in clinical practice, the MED3631-A/S has replaced the MED3631-A/M. Also, the distribution of radioactivity in the model MED3631-A/M "seed" was identical to the model MED3633 [103]Pd "seed". Therefore, five source geometries were modeled for the six sources studied.

For the sake of simplicity, only the geometry factors along the source transverse plane (e.g., $\theta_0=90°$) were calculated as would be needed to determine the radial dose function, g(r). For all source types, the voxels comprising the transverse plane were cubic with sides of 0.1 mm. The radioactive material of the three HDR sources was assumed to be uniformly distributed throughout their volumes; the distribution of radioactive material for the three "seeds" was assumed to be thinly deposited on the surface of the resin pads with a radial range of 0.24 to 0.26 mm. The geometry factors derived using Monte Carlo methods were compared with line source approximations for the three HDR sources. An exemplar MCNP input file is illustrated in FIG. 3; wherein the source long-axis was oriented in the x-direction (e.g., axs 100, cx 0.017) while the tally cell sampling space was aligned with the z-axis (e.g., pz 0.02 . . . pz 0.51). The geometry factor for the three sources containing resin beads as calculated using MCNP were compared with both a single-point source approximation and a multi-point source (n=4) approximation. The position of the origin for the single-point source approximation was set at the center of the "seed". The geometry factor derived using a multi-point source approximation was calculated from the sum of four-point source approximations, with each origin located at the center of each resin bead.

As there were no particle collisions or manipulations of material cross-section data, a great number of particles were calculated within a short period of time. Using MCNP on a PVM$_9$ distributed network of 6 computers, streaming of $1\times10^9$ isotropically-emitted particles was performed within a matter of hours. While this number of particles may seem excessive, the solid-angle subtended by the 0.1 mm cubic tally cell was relatively small and diminished with increasing distances. The number of particle histories could have been greatly diminished had variance reduction techniques been employed such that the direction of the particle emission was not isotropic but was biased towards the region of interest, or had the tally region been circumscribed by a torus (e.g., $2\pi$ about the transverse plane, instead of using simple cubes). The relative error for each of the five calculated geometry factors ranged from 0.1% for small distances, to 0.5% at a distance of 5 mm.

B. Results From the Application of the Mathematical Methodologies

Figure 2:
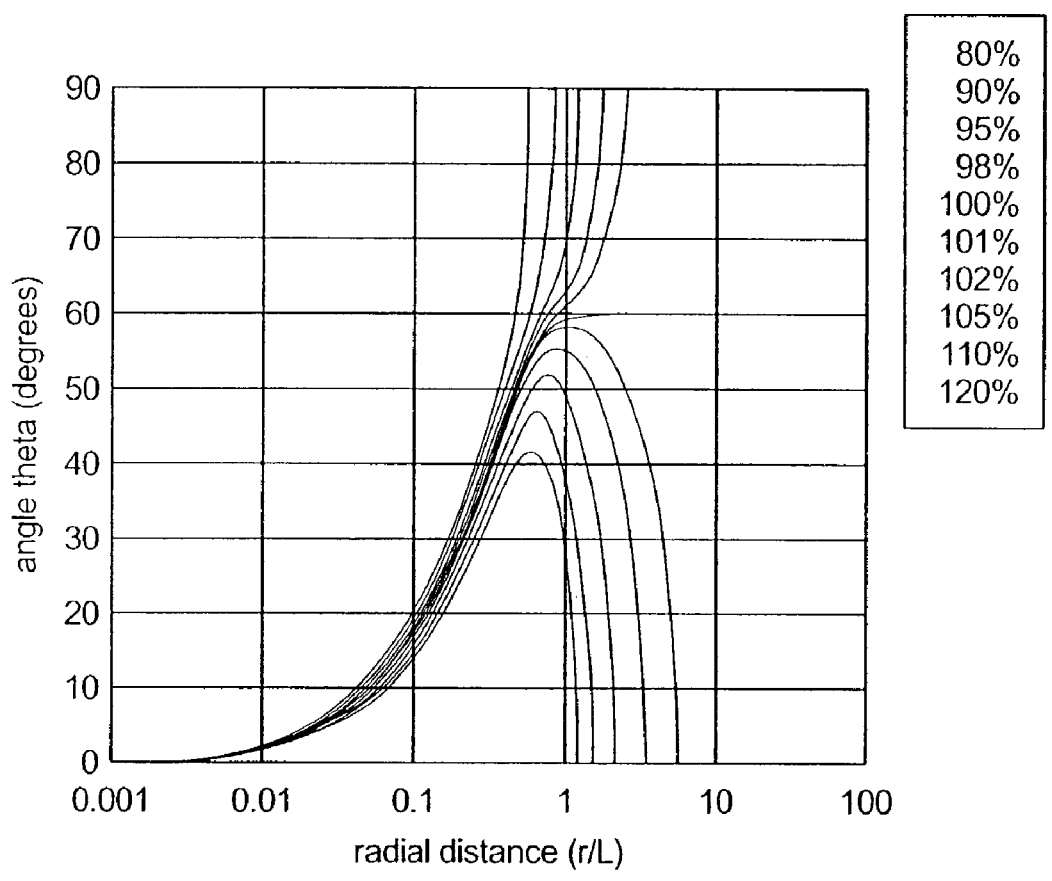
FIG. 2: illustrates the equivalence of the point and line source approximations with various errors. It is evident that these two approximations are within ±2% at θ=60° for dimensionless r/L ratios greater than 3.6. The top curve represents the 80% curve, wherein the line source approximation produces a geometry factor which is 80% of the value produced using a point approximation. The bottom curve signifies the 120% equivalence data.
Figure 4:
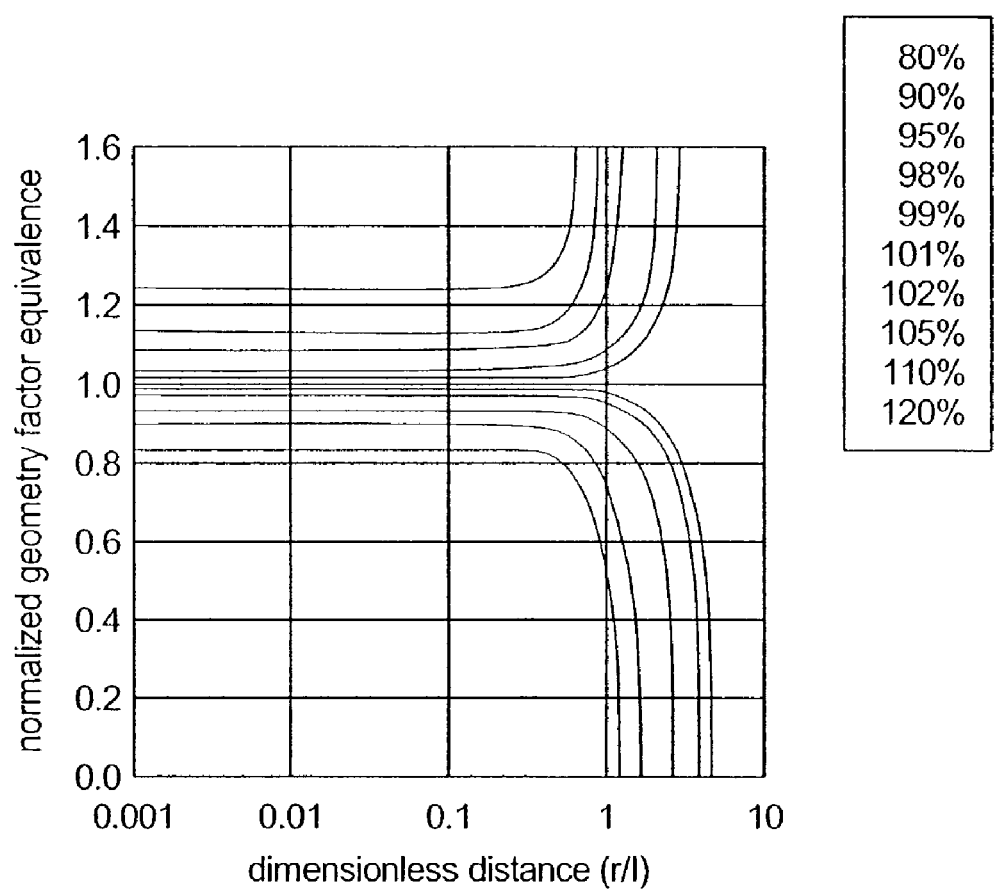
FIG. 4: illustrates the normalized geometry factor equivalence of point and line source approximations. The ratio of arbitrary equivalence of point- and line-source approximations are normalized to the 100% equivalence data. The arbitrary equivalence ranges from 80% (top curve) to 120% (bottom curve).

By examination of the center-curve illustrated in FIG. 2, it becomes evident that there exist locations in which the geometry factor determined with a line source approximation may be accurately characterized with a $1/r^2$ term. Also illustrated therein are curves in which the line source approximation is 1-, 2-, 5-, 10-, and 20%-less than or greater than the point source approximation. For an r/L value greater than approximately 2, these locations exist at $\theta=60°$, and $\theta=120°$ due to symmetry, from the line source long-axis. This approach may be useful for near-field dosimetry measurements of brachytherapy sources. Again by examination of FIG. 2, it is clear that if one uses the point source approximation at r/L ratios greater than about 3.6, errors in the geometry factor less than ±2% may be expected for all angles when using point and line source approximations. Those curves expressing errors from the equivalence of the point and line source approximations were normalized to the 100% equivalence curve in which there was no error. Similarly, from FIG. 4, it is apparent that the normalized values reach equilibria for r/L values less than 0.2.

1. Geometry Factors Derived Using Monte Carlo Methods

Figure 5:
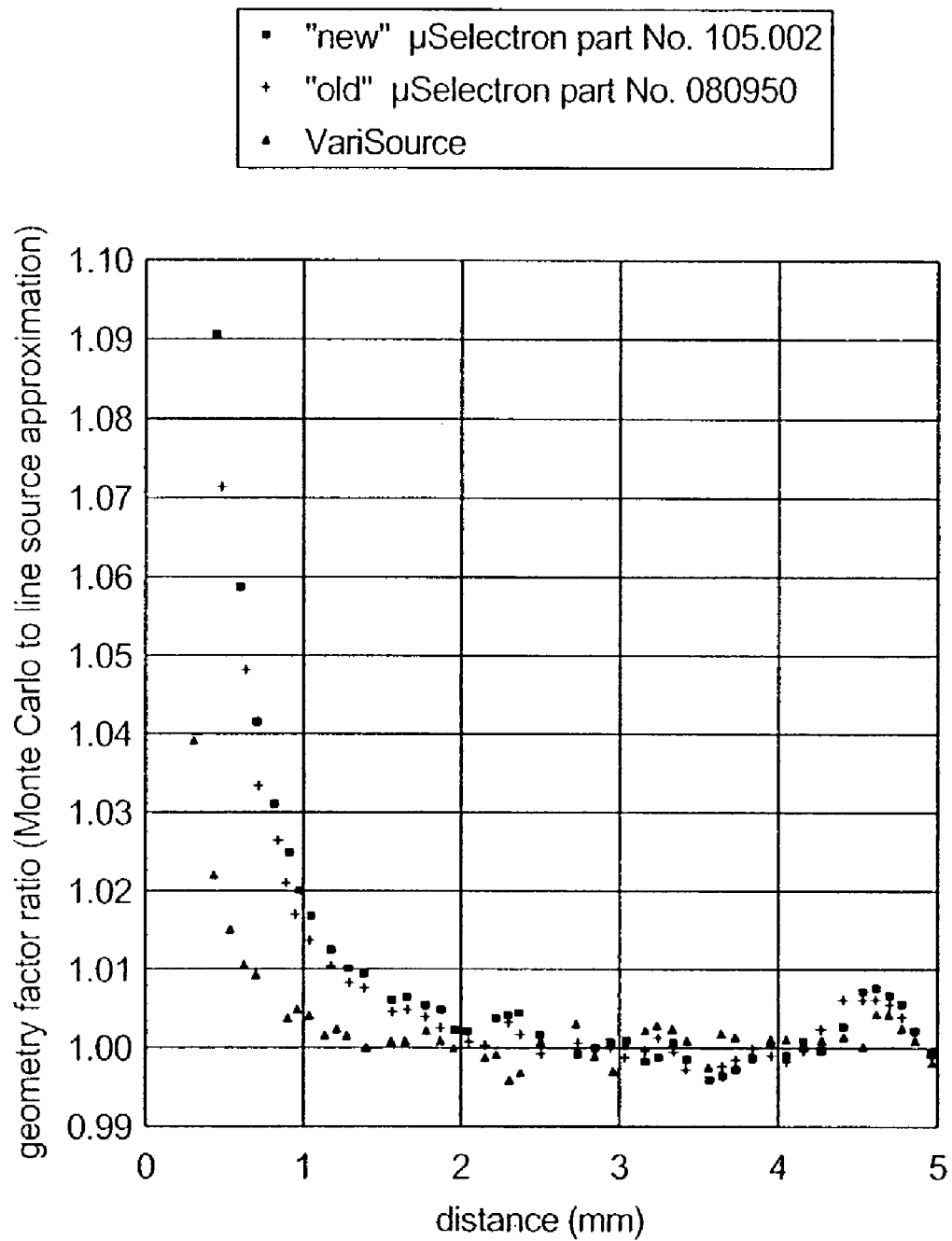
FIG. 5: illustrates the ratios of Monte Carlo-derived geometry factor to those obtained using a line-source approximation for three $^{192}$Ir HDR sources (μSelectron Models 080950 and 105.002; and VariSource). Upon examination of the figure, it is apparent that the line-source approximation significantly differs (i e., 2%) from the Monte Carlo-derived geometry factor at distances of approximately 0.5 and 0.8 mm along the transverse plane for the VariSource and the two μSelectron sources, respectively.
Figure 6:
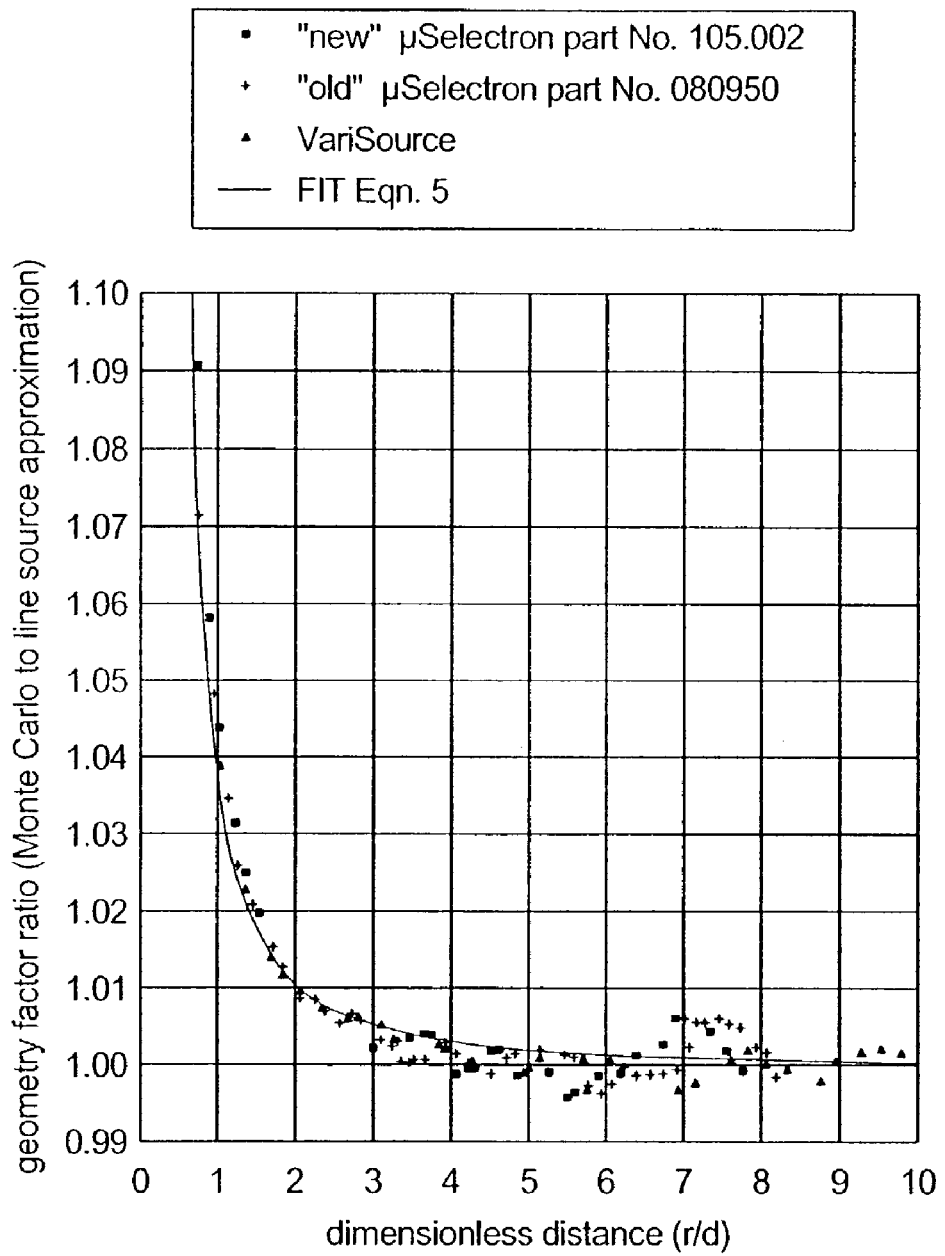
FIG. 6: illustrates the ratios of Monte Carlo-derived geometry factor to those obtained using a line-source approximation for three $^{192}$Ir HDR sources (μSelectron Models 080950 and 105.002; and VariSource), with distances, r, normalized to the diameter, d, of the active source active. The fitted curve (see, Equation 5) agrees with the calculated data presented within the relative errors (1σ). However, it should be noted that these relative errors increased for increasing r/d ratios.

FIG. 5 presents the ratios of geometry factors derived using Monte Carlo methods to those derived using line source approximations for the three HDR source types. From this data, it is clear that the line source approximation of the geometry factor significantly differs from the geometry factor obtained using Monte Carlo methods for distances less than 0.5 and 0.8 mm for the HDR VariSource and two shorter μSelectron HDR sources, respectively. The abscissa of each data set was divided by the corresponding active source length to yield a dimensionless parameter (r/d) in which all the data sets could be fit to a single curve. This curve took the form presented in Equation 5 where d is the diameter of the active source. From examination of FIG. 6, it is also evident that this equation well fit the three line source types examined herein for r/d ranging from 0.7 to 10. Until proven otherwise, it is not recommended to extrapolate this model for r/d distances less than 0.7.

$$\frac{G(r,\theta_0)_{MCNP}}{G(r,\theta_0)_{linesource\ approximation}} = e^{\left(\frac{\pi r}{d}\right)^{-2}} \quad (5)$$

Figure 7:
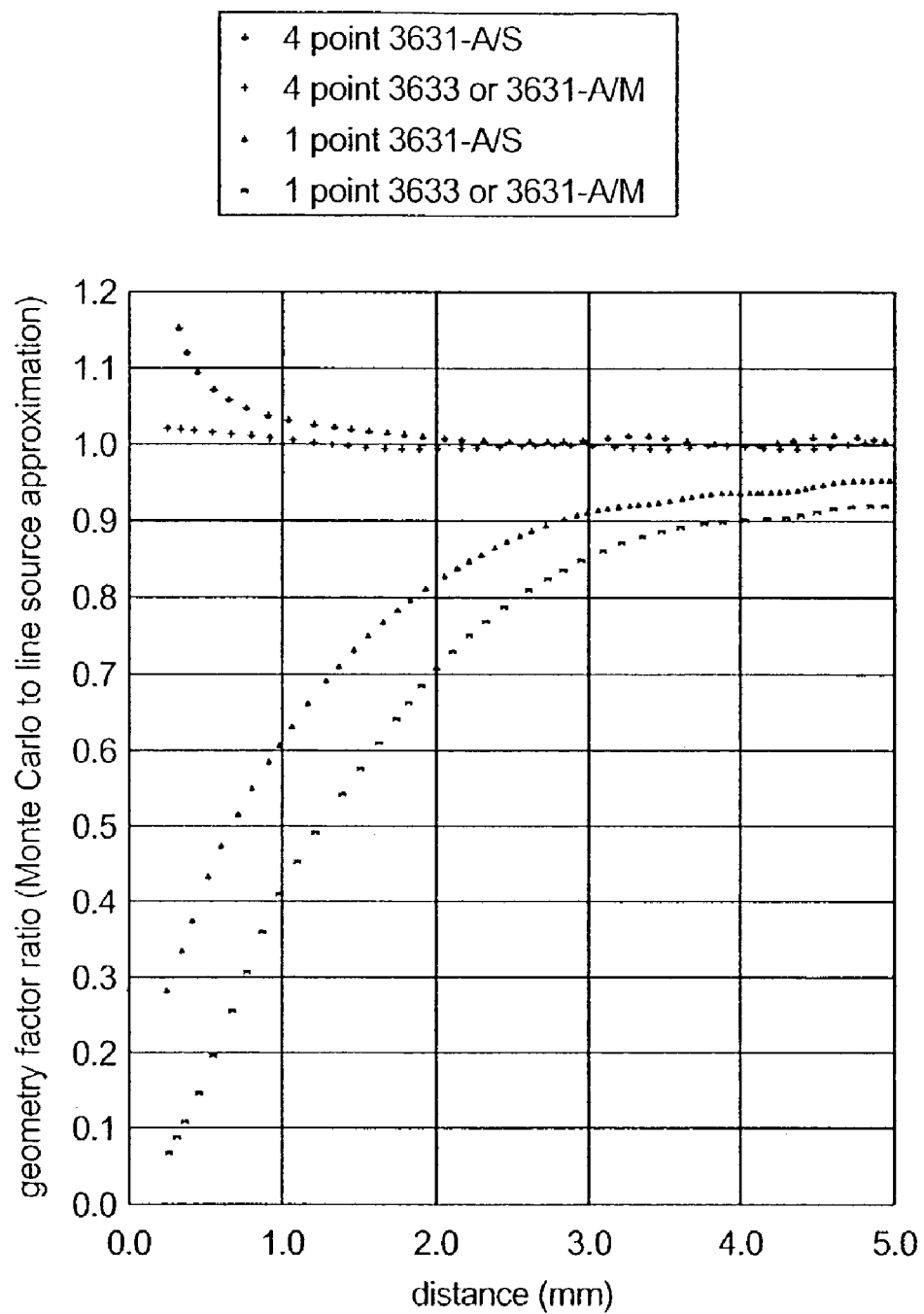
FIG. 7: illustrates the ratios of Monte Carlo-derived geometry factor to those obtained using multi-point (n=4) and single-point source approximations for $^{103}$Pd and $^{125}$I "seeds" produced by North American Scientific as distributed by Mentor Corporation. The multi-point source approximation is equivalent to the sum of four separate single-point source approximations where each source represents a polystyrene spheres as an ion exchange resin coated with either $^{103}$Pd or $^{125}$I. Due to the geometry being better represented by the multi-point source approximation, differences compared to the Monte Carlo-derived geometry factors are significantly less than those compared between the single-point approximation and Monte Carlo-derived geometry factors.

FIG. 7 presents the ratios of geometry factors derived using Monte Carlo methods to those derived using multi-point and single-point source approximations for the [103]Pd and [125]I "seeds" where individual resin beads were approximated as a point sources. It is apparent that the single-point source approximation of the geometry factor differs substantially from the geometry factor derived using Monte Carlo methods at distances less than 5 mm. Using the multiple-point (n=4) source approximation for the geometry factor, differences between the geometry factor derived using Monte Carlo methods become significant only at distances less than 1.0 and 0.3 mm for the MED3631-A/S and the MED3633:MED3631-A/M source geometry, respectively. For a given distance, r, these differences will increase as the $\theta$ varies from 90°, and it may be necessary to use Monte Carlo methods to solve the geometry factor for radial distances greater than 0.3 mm.

V. Application of the Mathematical Formalisms of the Present Invention in [252]Cf Brachytherapy The effective use of encapsulated radionuclides in brachytherpy ultimately requires accurate physical dosimetry for individual point or line sources. The objective of such dosimetry generally is to specify in detail the spatial distribution of absorbed dose rate in a tissue-like medium surrounding the source. Dose distributions for individual sources serve as input data for the design of implant configurations incorporating multiple sources and/or inert spacer material. The experimentally determined single-source distributions are combined, by computer-based computations, in evaluating the three-dimensional distribution within the treatment region. The use of such high-speed digital computing techniques makes it feasible to sum the contributions of many sources m determining the dose rate at each point.

The radiation oncologist and medical physicist strive to determine the dose to a high degree of accuracy at a point in or near an actual implant. As a criterion for accepting or rejecting a given source configuration, this figure is likely to be applied at the periphery of an implanted tumor, where the concern is to minimize damage to normal tissue. In view of the practical difficulties of source localization, tissue heterogeneity, and measurement accessibility—all of which unavoidably contribute heavily to dosimetric uncertainty in the clinical setting—it is reasonable to require that the component of error associated with predetermined single-source dose distributions be as accurate and reproducible as possible given this aforementioned difficulties. Failure to achieve this high degree of accuracy would make difficult the comparison of clinical results obtained in various, different medical centers.

In the present invention, a mathematical model using the product of the physical dose multiplied by the relative biological effectiveness (RBE) for that specific dose rate and anatomical site for both healthy and malignant tissues is incorporated into the source specification (e.g., g(r) and $\Lambda$), due to the fact that radiation from $^{192}$Ir and of $^{252}$Cf have markedly different biological responses and since a biological dose rate factor is not common in commercial treatment planning systems. For $^{252}$Cf the majority of physical dose, and large majority of biological effective dose is deposited by neutrons. Therefore, use of conventional clinical applicators (e.g., Fletcher-Suit for gynecological sites) with $^{252}$Cf is contra-indicated since the shielding material (e.g., tungsten or lead used to protect the bladder and rectum) is relatively ineffective for neutrons.

The dose distributions about $^{252}$Cf sources may be measured and calculated in a number of ways. For example, Monte Carlo modeling of $^{252}$Cf was first performed by Krishnaswamy in 1971, and later confirmed experimentally in 1972 using paired chambers measuring sources fabricated at SRL. See, Krishnaswamy, 1972. Calculated depth dose tables for $^{252}$Cf sources in tissue, *Phys. Med. Biol.* 17: 56–63; Colvett, et al., 1972. Dose distribution around a $^{252}$Cf needle, *Phys. Med. Biol.* 17: 356–364. Subsequently, more advanced means of neutron detection and modeling using foil activation techniques, chambers, and Monte Carlo N-Particle Transport Code System (MCNP) have confirmed Krishnaswamy's results while providing information about neutron spectra and near-source data. With the current advances in computer processing power, it is expected that $^{252}$Cf treatment planning will shift from "look-up" tables of along-away dose data to eventual full physics Monte Carlo modeling of the in vivo patient dosimetry.

Currently, no medical institutions within the United States are using $^{252}$Cf sources for tumor therapy. Neutron brachytherapy (i.e., insertion of the neutron source directly into or around the tumor) is markedly more effective than conventional photon radiotherapy in treating certain tumors, specifically bulky tumors and hypoxic (oxygen-deficient) tumors. For example, impressive results have been reported using $^{252}$Cf brachytherapy for advanced bulky gynecological tumors. See, Maruyama, et al., 1991. A review of californium-252 neutron brachytherapy for cervical cancer, *Cancer* 68: 1189. In addition, a recent workshop presented data on improved survivability for several types of bulky and recurrent tumors (e.g., head and neck, gynecological, rectal) from $^{252}$Cf brachytherapy followed by photon therapy, compared with photon therapy alone. See, Wierzbicki, 1996. Californium-Isotope for 21st century radiotherapy, NATO Advanced Research Workshop, Detroit, Mich., Apr. 24–28, 1996.

Generally, as previously discussed, physicians currently have available a 25-year-old brachytherapy source design called the Applicator Tube (AT), developed at Savannah River Laboratory (SRL), which are manually "loaded" into the patient and followed by treatment times of several hours. Accordingly, clinicians would like stronger sources to reduce treatment times, remotely implanted (i.e., afterloaded) sources to reduce dose to clinical personnel, and smaller sources which are more amenable to restricted treatment vicinities such as brain tumors.

After production in the neighboring High Flux Isotope Reactor, the Radiochemical Engineering Development Center (REDC) at Oak Ridge National Laboratory processes the national supply of $^{252}$Cf and encapsulates the $^{252}$Cf in sealed sources upon request. See, Martin, et al., 1996. Proposed californium-252 user facility for neutron science at Oak Ridge National Laboratory. Paper presented at the 3rd Topical Meeting on Industrial Radiation and Radioisotope Measurements and Applications, Raleigh, N.C., Oct. 6–9, 1996. REDC is currently developing new $^{252}$Cf brachytherapy sources, tailored to an existing gamma-source afterloader design, which possess high dose rates, but are small enough for treatment of highly localized neoplasms (e.g., the virulent brain tumor glioblastoma multiforme). Results of these studies have shown that increasing $^{252}$Cf loading of up to two-orders of magnitude in existing SRL source designs (such as the AT), with concentrations of $^{252}$Cf of $\geq 1$ mg, are achievable.

While the Radiation Therapy Committee of the AAPM Task Group No. 43 brachytherapy dosimetry protocol (see, Nath, et al., 1995. Dosimetry of interstitial brachytherapy sources: Recommendations of the AAPM Radiation Therapy Committee Task Group No. 43, *Med. Phys.* 22: 209–234) recommends specification of absorbed dose in water, californium 252 ("$^{252}$Cf") may be considered as a "special case" with respect to its neutron emitting capacity. Similar to that for external beam neutron therapy (see, ICRU Clinical neutron dosimetry, Part I: determination of absorbed dose in a patient treated by external beams of fast neutrons, International Commission on Radiation Units and Measurements (ICRU 45, Bethesda, Md., 1989)), the majority of clinical experience using $^{252}$Cf employed specification of absorbed dose to tissue instead of water (See, e.g., Awschalom, et al., 1983. A new look at displacement factor and point of measurement corrections in ionization chamber dosimetry, *Med. Phys.* 10: 307–313). As there is at least an 8% difference in the absorbed dose in tissue versus water, due to difference in the material neutron kerma coefficients (See, e.g., Caswell, et al., 1982. Kerma factors of elements and compounds for neutron energies below 30 MeV, *Intl. J Appl. Rad. Isot.* 33: 1227–1262; Rivard, et al., 1998. "Calculated variation in neutron spectra for water, brain, and muscle from a $^{252}$Cf point source," in *American Nuclear Society Radiation Protection and Shielding Division: Technologies for the New Century*, pp. 219–225 (ANS Inc., La Grange Park, Ill., 1998)) continuation of the aforementioned practice to learn from previous clinical experiences has been repeatedly suggested. Various advances in source fabrication techniques (See, e.g., Awschalom, et al., 1983. Kerma for various substances averaged over the energy spectra of fast neutron therapy beams: a study in uncertainties, *Med. Phys.*

10: 395–409) at ORNL have served to markedly increase interest in the mixed-field dosimetry of $^{252}$Cf AT medical sources.

In brief, for the present invention, the experimental mixed-field dosimetry of $^{252}$Cf Applicator Tube (AT) sources, and Monte Carlo calculations of the neutron dose from $^{252}$Cf sources in a variety of media are disclosed. Specifically, ionization chambers and a miniature GM counter were used to measure the total and photon dose, respectively, close to $^{252}$Cf AT-type sources. A brachytherapy neutron dosimetry protocol, similar to the external neutron beam formalism presented in ICRU 45 (ICRU Tissue substitutes in radiation dosimetry and measurement, International Commission on Radiation Units and Measurements Bethesda, (ICRU 44, Bethesda, Md., 1989)), was then formulated and is disclosed herein. Comparisons of experimental dosimetry were made with results of Colvett, et al. (1972. Dose distribution around a $^{252}$Cf needle, *Phys. Med. Biol.* 17: 356–364) and comparisons of Monte Carlo calculated neutron dosimetry were made with results of Krishnaswamy (1971). Calculation of the dose distribution about $^{252}$Cf needles in tissue, *Radiol.* 98: 155–160; 1972. Calculated depth dose tables for $^{252}$Cf sources in tissue, *Phys. Med. Biol.* 17: 56–63). Finally, the neutron kerma in a variety of materials (ICRU Tissue substitutes in radiation dosimetry and measurement, International Commission on Radiation Units and Measurements (ICRU 44, Bethesda, Md., 1989) and for varying depths within each material was calculated using Monte Carlo methods (MCNP; Briesmeister, 1997. MNCP—A General Monte Carlo N-Particle Transport Code System, Version 4B, LA-12625-M) and compared with other fast neutron sources (Awschalom, et al., 1983. Kerma for various substances averaged over the energy spectra of fast neutron therapy beams: a study in uncertainties, *Med. Phys.* 10: 395–409).

A. Experimental Ion Chambers

Two types of TE ion chambers and a miniature GM counter were used as dosimetry equipment in the development of the present invention. Measurements of SRL- and ORNL-made $^{252}$Cf AT source dosimetry were made using a dosimetry protocol based on the ICRU 45 protocol for external neutron beam dosimetry (ICRU Clinical neutron dosimetry, Part I: determination of absorbed dose in a patient treated by external beams of fast neutrons, International Commission on Radiation Units and Measurements (ICRU 45, Bethesda, Md., 1989).

1. TE Ion Chambers

For calibration of ORNL-made $^{252}$Cf AT source strengths, two types of TE ion chambers were used. The first type was manufactured by Far West Technology Inc. (FWT, Model IC-17) and had a collecting volume of approximately 1 cm$^3$. The second chamber (Exradin; Model T1) had a 0.05 cm$^3$ collecting volume. Both chambers were comprised of A-150 TE plastic with methane-based TE gas flowing through each chamber. The TE gas was comprised of 3.2% $N_2$, 63.8% $CH_4$, and 33.0% $CO_2$ by volume. A single Matheson type flow meter was used with a setting of 9.1 cm$^3$/minute for controlling and monitoring the TE gas flow through each chamber. This flow rate displaced air within the chambers, yet did not cause over-pressurization.

Each chamber was placed in a 54 liter (28.6×30.8×61.1 cm$^3$) thin-walled plastic water phantom. A plastic jig was used to centrally position each ion chamber among a circumferential array of AT sources with the chamber stem and source transverse axes parallel. The ion chambers were generally positioned such that measurements would obtain "away" data as the center of the ionization chamber collecting volume was placed at the active source mid-plane height. However, off-axis measurements were also taken using the smaller Exradin chamber due to its smaller collecting volume for better spatial discrimination. A high voltage bias of approximately +500 volts was obtained from a power supply (Canberra; Model #3102). A digital electrometer (Keithley; Model 3561 7BBS) was used to measure the integrated charge over time, and the programmable time option (i.e., 1 minute) was used for consistency. Determination of charge leakage was measured before data was taken. Repeated, one minute readings were taken to establish reproducibility.

2. Miniature GM Counter

A miniature GM counter (FWT, Inc.; Model GM-1s) was used to discriminate photon dose from the total dose as determined with the TE chambers. Due to its construction and the $^{252}$Cf neutron energies, the miniature GM counter was found to be less sensitive to neutrons than to photons. See, e.g., Lewis and Hunt, 1978. Fast neutron sensitivities of Geiger-Mueller counter gamma dosimeters, *Phys. Med. Biol.* 23: 888–893). GM counter photon sensitivity was determined through calibration with a Cesium 137 ($^{137}$Cs) source. The same water phantom and experimental setup as used with the TE chambers was used; counts were integrated for 100 seconds using a scaler. Additionally, a lithium fluoride (LiF) cap was used in $^{252}$Cf experimental measurements so as to mitigate the effect of thermal neutrons. This approach, as compared to other methodologies utilizing paired chambers (e.g., A-150/TE and Mg/Ar chambers) was chosen due to the fact that the GM counter was less sensitive to low energy neutrons than the magnesium chambers. See, ICRU Clinical neutron dosimetry, Part I: Determination of absorbed dose in a patient treated by external beams of fast neutrons, *International Commission on Radiation Units and Measurements* (ICRU 45, Bethesda, Md., 1989).

B. A $^{252}$Cf Brachytherapy Dosimetry Protocol

The present invention discloses a methodology utilized to derive a modem dosimetry protocol similar to ICRU 45 (ICRU Clinical neutron dosimetry, Part I: Determination of absorbed dose in a patient treated by external beams of fast neutrons, *International Commission on Radiation Units and Measurements* (ICRU 45, Bethesda, Md., 1989)) with parameters which were expressly selected for $^{252}$Cf mixed-field dosimetry. $^{252}$Cf, as a radiation source, is unique as its fast neutrons possess relatively low energy and there is an appreciable photon dose component. In a mixed neutron-photon radiation field, the neutron and photon absorbed dose components may be determined from measurements made with two dosimeters. Since dosimeters which are sensitive to neutrons or photons alone, are not currently available, it was necessary to use two dosimeters with differing sensitivities to either neutrons and photons. The response of each dosimeter was found to be related to the neutron and photon absorbed dose components in the following equations:

$$R_T' = k_T D_N + h_T D_G, \quad (6)$$

$$R_U' = k_U D_N + h_U D_G, \quad (7)$$

where, $R_T'$=response of a dosimeter having approximately the same sensitivity to neutron and photon dose, divided by the chamber sensitivity used for calibration [cGy]

$R_U'$=response of a dosimeter having lower sensitivity to neutron than to photon dose, divided by the chamber sensitivity used for calibration [nC]

$k_T$=relative neutron sensitivity of a dosimeter having approximately the same sensitivity to neutron and photon dose [dimensionless]

$k_U$=relative neutron sensitivity of a dosimeter having lower sensitivity to neutron than to photon dose [dimensionless]

$h_T$=relative photon sensitivity of a dosimeter having approximately the same sensitivity to neutron and photon dose [dimensionless]

$h_U$=relative photon sensitivity of a dosimeter having lower sensitivity to neutron than to photon dose [dimensionless]

$D_N$=fast neutron dose [cGy]

$D_G$=total photon dose [cGy]

Accordingly, from Equations 6 and 7, the total dose may be determined as set forth in Equation 8. See, Broerse, et al., 1981. European protocol for neutron dosimetry for external beam therapy, *Brit. J. Radiology* 54: 882–898).

$$D_T = D_N + D_G = M_T (\Pi k_M)_T N_X A_{WALL} (f_i)_c d_T \frac{1}{k_T} \frac{1}{1+\delta}, \quad (8)$$

where, $D_T$=total (neutron+photon) absorbed dose [cGy]

$M_T$=raw electrometer reading [nC]

$(\Pi k_M)_T$=product of total correction factors [dimensionless]

$N_x$=exposure calibration factor in $^{60}$Co [R/nC]

$A_{WALL}$=wall absorption correction factor [dimensionless]

$(f_i)_c$=exposure-to-absorption does to reference issue correction factor [cGy/R]

$d_T$=replacement correction factor due to perturbation of the secondary charged particle energy fluence determined by replacing the phantom material with the ionization chamber [dimensionless]

$k_T$=relative neutron sensitivity of TE chamber [dimensionless]

$\delta$=response correction factor accounting for difference in response of TE chamber for neutrons and photons [dimensionless]

$$\delta = \frac{D\gamma}{D_N + D_\gamma} \frac{h_T - k_T}{k_i}. \quad (9)$$

In the protocol which follows, the dosimeter having approximately the same sensitivity to neutron and photon dos was an A-150 TE ion chamber while the dosimeter having lower sensitivity to neutron than to photon dose was the miniature GM counter. The relative neutron sensitivity of each TE chamber, $k_T$, was derived using Formula 3.9 set forth in the ICRU 45 protocol, and is presented infra in Equation 10. Using this formalism with appropriate values for $^{252}$Cf sources, the total dose may thus be determined.

$$\frac{1}{k_T} = \frac{(r_{A-150\,TE\,GAS})_n}{\left[\left(\frac{L}{\rho}\right)^{A-150}_{TE\,GAS}\right]_c} \frac{W_N}{W_C} \frac{(K_{MUSCLE}/K_{A-150})_n}{\left[\left(\frac{\mu_{en}}{\rho}\right)^{MUSCLE}_{A-510}\right]_c}, \quad (10)$$

where:

$(r_{A-150,TE\,GAS})_n$=A-150 wall to TE gas absorbed dose conversion factor [dimensionless]

$L/\rho$=ratio of mean restricted mass collision stopping power for A-150 plastic ion chamber wall and TE gas [dimensionless]

$W_N$=energy per ion pair for $^{251}$Cf neutrons [J/C]

$W_C$=energy per ion pair for $^{60}$Co [J/C]

$K_{MUSCLE}$=neutron kerma in ICRU muscle [J/kg]

$K_{A-150}$=neutron kerma in A-150 dosimeter wall [J/kg]

$\mu_{en}/\rho$=mass-energy absorption coefficient for ICRU muscle or A-150 plastic ion chamber wall [cm$^2$/g].

1. Monte Carlo Calculations

Neutron kerma was calculated with a distributed computing environment (Geist, et al., PVM: Parallel Virtual Machine—A User's Guide and Tutorial for Networked Parallel Computing (The MIT Press, Cambridge, Mass., 1994); Van den Heuvel, et al., 1997. Implementation of distributed computing for Monte Carlo simulations using PVM in a low tech environment, *Med. Physics* Obninsk, Russia, 90–91; Rivard, et al., Calculations of the $^{252}$Cf neutron spectrum in water for various positions and loadings of $^{10}$B and $^{157}$Gd, in American Nuclear Society Radiation Protection and Shielding Division: Technologies for the New Century, edited by D. T. Ingersoll (ANS Inc., La Grange Park, Ill., 1998), pp. 211–218) using MCNP (Briesmeister, 1997. MCNP—A General Monte Carlo N-Particle Transport Code System, Version 4B, LA-12625-M)) for a total of eleven different materials including: water, the synthetic muscle substitute—A-150 plastic, PMMA, brain, muscle, fat, pancreas, lung, bone, skin, and blood. The various elemental composition and mass densities of the aforementioned materials were taken from ICRU 44 (ICRU Tissue substitutes in radiation dosimetry and measurement, International Commission on Radiation Units and Measurements Bethesda, (ICRU 44; Bethesda, Md., 1989)) and the CRC Handbook (*CRC Handbook of chemistry and physics*, 65th edition (CRC Press Inc., Boca Raton, Fla., 1985). Each material subtended a 15 cm diameter spherical phantom in which a centrally-placed, isotropic neutron point source was positioned. Neutron kerma for each material was calculated for radii ranging from 0.1 to 5.0 cm. Transport of at least 1×10$^7$ particles was necessary to achieve relative errors (1σ) of 0.1%. Absorbed dose from neutrons was calculated using the MCNP P6 heating tally which determined kerma in the material of interest based on energy deposition and microscopic cross-sections. In this method, the integral of energy deposition over all energies was found to be equal to the total energy absorbed within a volume element (voxel). To obtain absorbed dose, the energy deposited in a given voxel was divided by the mass of the voxel.

The $^{252}$Cf prompt neutrons were modeled with an isotropic Maxwellian neutron energy spectrum as presented in Equation 11, supra. Use of this model was found to be more representative of the $^{252}$Cf neutron energy spectrum than a Waif fission spectrum. See, Marten, et al. 1990. The $^{252}$Cf (sf) neutron spectrum in the 5-to 20-MeV energy range, *Nuc. Sci. Eng.* 106: 353–366; Chalupka, et al., 1990. Results of a low background measurement of the fission neutron spectrum from $^{252}$Cf in the 9- to 29-MeV energy range, *Nuc. Sci. Eng.* 106: 367–376. The non-normalized neutron energy spectrum, N(E), is given in Equation 6 where E has units MeV and 1.42 is a fitting parameter.

$$N(E) = e^{-E/1.42} E^{1/2}. \quad (11)$$

VI. Specific Examples of $^{252}$Cf Dosimetry

A. Calculation of Radiation Transport and Dosimetry

Radiation transport and dosimetry were calculated using MCNP (See, e.g., Briesmeister, MCNP—A General Monte Carlo N-Particle Transport Code System, Version 4B, LA-12625-M (1997)) simultaneously on six computers, thus providing a distributed, networked computational environment. The merit of this approach is that calculations may be performed in less time than if only a single computer were utilized. To the Applicant's knowledge, MCNP is the only widely distributed neutron transport code possessing this capability. The following section will provide a brief overview of the parallel virtual machine (PVM; Geist, et al. PVM: Parallel Virtual Machine—A User's Guide and Tutorial for Networked Parallel Computing (The MIT Press, Cambridge, Mass., 1994)) concept, as well as a description of its application for this study.

PVM is a UNIX-based program available as "Free-Ware" over the Internet. Specifically, PVM versions 3.3.11 and 3.4 were utilized for distributing Monte Carlo calculations in the present invention. MCNP is written in FORTRAN 77, and consequently requires a compiler to create the executable program. During the compilation stage, one may select the distributed processing option where the computer in question becomes either a master or slave; typically the master computer should be the most powerful. When performing calculations, a PVM daemon is created by the master computer on the slave computer using a remote shell rsh configuration to distribute processing needs for hastened calculations. The following command is typically utilized when starting the PVM program: pc93% pvm hostfile. In the hostfile file, a list is made of user logon names lo, paths to each PVM daemon dx and executable program ep, and computer speed sp ratings. If one of the computers in the cluster should hang-up or be powered down, or if the network connection between the slaves and master should be interrupted, the system will continue to calculate and will compensate for the missing computer. Load-balancing and fault tolerance are features which enhance compatibility between MCNP and PVM, and make distributed MCNP a feasible tool as previously (before MCNP 4B) the system would crash and all pre-dump calculative information would be lost. Total expenditures for the software are on the order of as little as $250.00, including MCNP4B, the atomic and nuclear cross-section data libraries, and the PVM software.

To optimize the computer cluster performance to minimize time for Monte Carlo calculations, the optimal sp value for spawning processes on each computer was sought. Runs were performed using $1 \times 10^9$ particle histories. These optimization efforts were conducted when no other significant competing processes were running and determined by subtracting out the startup time necessary for processing of both the MCNP input code and cross-section data libraries. This configuration is presented in Table 12. It was later realized that the PVM sp command is not used by distributed MCNP, and automatic load balancing for the computer cluster could be obtained through utilization of the following command: pc93% mcnp i=rivard tasks 6. Here, an MCNP input file (rivard) is used to initiate an MCNP run on the master computer (pc93), and the integer following the tasks command indicates the number of computers (i.e., 6) within the cluster. Use of a positive tasks integer indicates automatic load balancing where requests for calculation packets for each computer are managed by the PVM daemon; the fastest computers request additional Monte Carlo calculations more frequently than the slower computers. If a negative tasks integer had been utilized, the relative speed weighting of all computers would have been made equal and, like the concept of the weakest link in a chain, completion of the entire Monte Carlo run would be delayed by the slowest computer finishing its share of calculations. Applying the positive tasks integer technique permitted calculations to be performed approximately 25-times faster than had a negative integer been employed. For example, although each computer was not the current "state-of-the-art", the combination of six computers performed calculations at a rate approximately 2-times that of a CRAY J-90 supercomputer, when couched in terms of actual user-time. However, it should be noted that only 6% of the J-90 processing resources were available to the user at the time of comparison. This value is typical for such a shared, parallel machine.

It is important to note that one of the computers (i e., sgi_2) is occasionally used for treatment planning of both $^{192}$Ir HDR brachytherapy and $^{125}$I prostate permanent implants. Therefore, it was imperative after every calculation run was initiated that efforts were made to not compete with timely clinical computational jobs. This was achieved through lowering the process priority of the recently initiated MCNP run. In practice, lowering of the process priority was executed through entry of a simple UNIX command (e.g., sgi_2 renice 15-p 12345) where 15 is the new priority setting and 12345 is the process identification number. Reprioritization of the distributed calculation run on the sgi_2 computer resulted in a transparent utility which could effectively calculate radiation transport and posed no problems in over two years of operation. This reprioritization scheme was also used on the pc25 and pc93 computers as they are private workstations of departmental physicists.

During the course of a normal business day, this distributed network utilized an average of 98% of the available processing power. The computers were virtually 100% utilized during non-business hours (12 hours/day) and during the weekends. Thus, for extended calculation runs (clock time>1 day) in which results are not immediately necessary, distributed MCNP using PVM software may be considered a resourceful utility for radiation treatment planning calculations. In late-1999, MCNP version 4C will be available with added features such as extended energy ranges and improved neutron physics modeling of unresolved resonance regions. While ($\gamma$,n) transport is not currently available, the utility of MCNP/PVM is underscored upon realizing that MCNP can not only transport neutrons as discussed herein, but may also couple transport of electrons, photons, and neutrons for a given calculation.

B. Dose Calibration Measurements

An accessible instrument for assaying source strength within the clinic is a dose calibrator. Here, a radioisotope dose calibrator (Capintec; Model CRC-5) was used with the previously described SRI-made and ORNL-made $^{252}$Cf AT sources. Relative measurements of source strength were performed for these two source types. A low mass jig was used to position the $^{252}$Cf AT sources at the center of the large collecting volume with parallel long axes. Stability and rigidity of the positioning jig constrained all source types within 1 mm of the collecting volume center. The dose calibrator sealed collecting volume was filled with argon gas at a stated pressure of 2.03 MPa (20 atmospheres). As only relative measurements were made, the calibration dial was set such that 1 µg of $^{252}$Cf source strength was equal to 1.000 multiplied by the reading (Rdg) when using SRL-made $^{252}$Cf AT sources as presented in Table 13. Illustrated in Table 14 are the dose calibrator measurements of ORNL-made AT source strengths. The same setup was used for both the SRL-made AT sources, and measurements were performed on the same date within a matter of hours to negate radioactive decay effects. Reproducibility was typically ±0.1% for both source types; a fixed calibration setting of 823 was used to correlate the reading (Rdg) with $^{252}$Cf source strength.

Examining the dose calibrator results for the SRL-made and ORNL-made $^{252}$Cf AT sources in Tables XIII and XIV, respectively, it appears that precision on the order of ±0.3% may be expected for relative source strength measurements with this detector and experimental setup. The fabrication techniques of the SRL-made and ORNL-made sources differ slightly in that the SRL-made $^{252}$Cf active element had three active source wires to provide improved batch uniformity among the twelve sources. The active element of each ORNL-made AT source was comprised of a single wire. See, Rivard, et al., 1999. Clinical brachytherapy with neutron emitting $^{252}$Cf sources and adherence to AAPM TG-43 dosimetry protocol, *Med. Phys.* 26: 87–96. Consequently, the variation in batch uniformity of the ORNL-made AT sources was slightly larger than for the SRI-made sources.

Although the majority of absorbed dose from $^{252}$Cf AT sources is imparted by neutrons, the dose calibrator was inherently more sensitive to the approximately 1 MeV photon emissions than from neutrons due to the argon gas collecting volume and metallic housing. See e.g., Skarsvag, 1986. Differential angular distribution of prompt gamma-rays from spontaneous fission of $^{252}$Cf, *Phys. Rev.* 22: 638–650 (1986). Since approximately half of the photons emitted from $^{252}$Cf sources originate from spontaneous fission decay products, it is likely that the spontaneous fission decay products were generally in equilibrium with the as the 2.645 year half life was used to decay the SRL and the ORNL-made source strengths used for comparison. This equilibrium following a four year period is supported by the average μg/Rdg ratios for the SRL-made (1.000) and ORNL-made (1.001) AT sources. While relative measurements of $^{252}$Cf AT source strengths using a dose calibrator were in ±0.1% agreement with that predicted by radioactive decay using a $^{252}$Cf half life of 2.645 years, the precision using such a device was only ±0.3%.

C. Experimental Studies

1. Ion Chamber Calibration

Before measurements of $^{252}$CF sources was initiated, the exposure calibration factor ($N_x$) for each chamber was determined with a clinical $^{60}$Co radiation source. Results of these calibrations are presented in Table 1. As the T1 chamber had a volume approximately 5% of the two IC-17 chambers, its $N_x$ was expected to be approximately 20-times greater. Interestingly, however, experimental analysis determined that the T1 $N_x$ was only approximately 15-times larger than for the average IC-17 $N_x$ value. Measurements of the system leakage showed none of the ion chambers produced leakage currents exceeding $1 \times 10^{-15}$ A.

2. GM Counter Calibration

Specific to the GM counter, measurement of the dead-time was required as this instrument was used in "pulse mode" instead of the "current mode" as utilized in the measurements obtained in the other 5 chambers. By use of a digital oscilloscope (Tektronix Model 2440), the dead-time was measured visually through identification of ensuing random pulses as 25–30 μs. Results were obtained using both $^{252}$Cf and $^{137}$Cs sources, and there was no discernable difference in measured dead-time with the use of either isotope. The FWT calibration data (circa 1985) stated a dead-time of 30.6 μs. Calibration was performed at distances of from 15 to 50 cm from a 122 mCi (4.51 MBq) $^{137}$Cs source. With the non-paralyzable model (Knoll, General properties of radiation detectors, in Radiation detection and measurement, 2nd edition (John Wiley & Sons, New York, 1989), pp. 103–130) the true count rate (n) could be calculated from the measured count rate (m) and knowledge of the 30.6 μs dead-time (t) by use of Equation 12); background count rate was subtracted from all readings. A calibration factor of $5.10\pm0.11\times10^7$ cGy/count, was determined with a $^{137}$Cs F of 3.25 R-cm$^2$/mCi-h, $\mu_{en}/\rho$ muscle to air ratio of 1.10, and photon W/e value of 33.97 J/C, $$n = \frac{m}{1 - m\tau}. \qquad (12)$$

3. TE Ion Chamber Results

It was necessary to provide specific values for all of the parameters in Equations 8 and 10 to obtain the $^{252}$Cf total dose as measured using the FWT and Exradin TE ion chamber current readings. Many parameters are recommended by ICRU 45 (ICRU Clinical neutron dosimetry, Part I: Determination of absorbed dose in a patient treated by external beams of fast neutrons, *International Commission on Radiation Units and Measurements* (ICRU 45, Bethesda, Md., 1989)) and are independent of the neutron source. Generally, an $A_{WALL}$ value of 0.983 for the FWT IC-17 chambers and 0.992 for the Exradin T1 chamber is recommended. See, Gastorf, et al., 1986. Cylindrical chamber dimensions and the corresponding values of $A_{WALL}$ and $N_{GAS}/(N_x A_{ion})$, *Med. Phys.* 13: 751–754). Similarly, the exposure-to-absorbed dose to reference tissue correction factor, $(f_t)_c$, was determined to be 0.966. Also according to ICRU 45, the value of the $\mu_{en}/\rho$ ratio for ICRU muscle and A-150 plastic is 1.001.

A value of $(r_{m\ \ \ g})_n/[(L/\rho)_m/(L/\rho)_g]_c = 1.00\pm0.02$, is recommended by ICRU 45 for neutrons. The product of total correction factors, $(\Pi k_M)T$, was reduced to 1.0291, with $C_{TP}$ (1.025) and $C_{el}$ (1.004). The energy necessary to produce an ion pair in methane-based gas when irradiated by $^{60}$Co is 29.3 eV. For recoil protons from $^{252}$Cf neutrons, the energy per ion pair was calculated to be 31.65 eV based on convolving the $^{252}$Cf neutron energy in ICRU muscle with methane-based TE gas data originally determined by Goodman and Coyne (1980. $W_n$ and neutron kerma for methane-based tissue-equivalent gas, *Radiat. Res.* 83: 491). The $W_N/W_C$ ratio was found to be 1.080 for $^{251}$Cf in methane-based TE gas. The ratio of the kerma for ICRU muscle to A-150 plastic was calculated to be 0.958, which did not change significantly with the overall distance from the radioactive source ranging from 0.5 to 5.0 cm. By substitution of the aforementioned parameters in Equation 10, a value of $0.969\pm0.02$ for $k_T$ was obtained. It should be noted that this value was within 1% of the 0.96 $k_T$ value for neutrons with energy between zero and 5 MeV as determined by Waterman, et al. (1979. Energy dependence of the neutron sensitivity of C—CO$_2$, Mg—Ar, and TE-TE ionisation chambers, *Phys. Med. Biol.* 24: 721).

The ratio of photon dose to total dose ranged from 25% to 40%, with higher values occurring at larger distances. See, e.g., Colvett, et al., 1972. Dose distribution around a $^{252}$Cf needle, *Phys. Med. Biol.* 17: 356–364; Anderson, 1973. Status of dosimetry for $^{252}$Cf medical neutron sources, *Phys. Med. Biol.* 18: 779–799; Anderson, 1986. $^{252}$Cf physics and dosimetry, *Nuc. Sci. App.* 2: 273–281; Yanch and Zamenhof, 1992. Dosimetry of $^{252}$Cf sources for neutron radiotherapy with and without augmentation by boron neutron capture therapy, *Rad. Res.* 131: 249–256. For distances of 1.0, 2.0, 3.0, and 5.0 cm, the ratio of photon to total dose was found to be approximately 32%, 33%, 36%, and 44%, with values of 0.010, 0.011, 0.012, and 0.014 for δ. The value of $h_r$ was unity. Using a fixed value of 0.011 for δ, the above-referenced parameters were incorporated into Equation 8, without the demonstration of significant radial dependence.

ICRU 45 defines the displacement correction factor ($d_r$) to account for differences in absorption and scattering of the primary radiation field due to replacing the phantom material with the gas cavity in the ion chamber. While it has been shown that for low energy neutrons and for small chambers that $d_T$ may be assumed to be unity (Zoetelief, et al., 1980. Effect of finite size of ion chambers used for neutron dosimetry, *Phys. Med. Biol.* 25: 1121) it is possible to separate a correction factor from this term which accounts for the dose gradient in the phantom (Awschalom, et al., 1983. A new look at displacement factor and point of measurement corrections in ionization chamber dosimetry, *Med. Phys.* 10: 307–313). This effect was contemplated in the present invention as it is possible to orient the $^{252}$Cf sources in such a way that there are no dose gradients. Measurements of dose gradient were conducted for both chamber types through laterally offsetting each chamber by 5 mm. Within experimental uncertainties of these measurements, ±1%, the dose gradient correction factor may be assumed unity for both chambers. For the IC-17 chambers, Equation 8 may be simplified, thus yielding Equation 13. The value of 0.967±0.008 differs by only +1.4% of the value (0.954) originally determined by Colvett, et al. (1972. Dose distribution around a $^{252}$Cf needle, *Phys. Med. Biol.* 17: 356–364). Accordingly, the total dose for the transverse-axis was calculated for each TE chamber, and is presented in Table 2 along with those values derived by Colvett, et al. and Krishnaswamy (1972. Calculated depth dose tables for $^{252}$Cf sources in tissue, *Phys. Med. Biol.* 17: 56–63).

$$D_T = 0.967 M_T (\Pi k_M)_T N_X. \tag{13}$$

It should be noted, however, that the dosimetry data obtained by Colvett, et al. and Krishnaswamy were derived utilizing an SRL-made needle source which was constricted in a markedly different manner than that of the SRL-made or ORNL-made AT sources. The T1 chamber had the smallest collecting volume of the chambers available, and was used to measure off axis dosimetry. Using the same dosimetry formalism as for the transverse-axis, the total dose was also determined. These results, illustrated in Table 3, are compared with the data of Colvett, et al. and Krishnaswamy. As shown in Table 4, misalignment of the T1 chamber on this axis by 4–6 mm led to errors of 4 to 8%. While it was a straightforward task to centrally-position the chambers within the circumferential array of the AT sources, proper alignment of the chambers along the long-axis of the AT source was initially found to be problematic, as there were no outside demarcations on either the AT sources or the T1 chamber buildup cap. Therefore, it was necessary to manually scan the T1 chamber in the "along" axis in order to determine the centerline position; wherein negative "along" values were towards the AT Bodkin eyelet-end.

4. GM Counter Results

At an energy of approximately 4 MeV, an average $k_U$ value of 0.6%±0.2% was adopted for the five different GM counter types utilized in the present invention. Previously published results (Jones, The neutron sensitivity of a GM counter between 0.5 and 8 MeV, in: *Radiation Protection, 4th Symposium on Neutron Dosimetry*, edited by G. Burger and H. G. Erbert (EUR 7448, Munich, Germany, 1981), pp. 409–419) had only determined the $k_U$ value (0.05%±0.05%) of a single GM counter type (i.e., ZP 1320) for energies less than 1 MeV.

By use of previously published data of the $^{252}$Cf neutron energy spectrum (see, Rivard, et al., Calculated variation in neutron spectra for water, brain, and muscle from a $^{252}$Cf point source, in: *American Nuclear Society Radiation Protection and Shielding Division: Technologies for the New Century*, edited by D. T. Ingersoll, ANS Inc., La Grange Park, Ill., 1998, pp. 219–225) and various other studies (Lewis and Hunt, 1978. Fast neutron sensitivities of Geiger-Mueller counter gamma dosimeters, *Phys. Med. Biol.* 23: 888–893), the GM-1s $k_U$ value was inferred to be 0.2±0.2%. Additionally, when accounting for measurement reproducibility and systematic uncertainties, a $k_U$ value of zero may be used. Measured GM-1s photon dose results (see, Table 5) were obtained using the calibration factor of $5.10 \times 10^{-7}$ cGy/count, the dead-time correction of Equation 12, and a $k_U$ value of zero. The $^{252}$Cf neutron dose (see, Table 6) was obtained by subtracting the photon dose measurements taken with the GM-1s counter (see, Table 5) from the total dose determined with the T1 chamber and average of the two IC-17 TE chambers (see, Table 3).

D. Calculative Results

Table 7 presents the neutron kerma for a total of 11 different types of materials which were measured at a clinically-relevant radial distance of 1.0 cm. It should be noted that $^{252}$Cf neutron kerma is normalized to muscle at a distance of 1.0 cm for comparison with dosimetry properties of other neutron sources normalized to muscle. See, Awschalom, et al., 1983. Kerma for various substances averaged over the energy spectra of fast neutron therapy beams: a study in uncertainties, *Med. Phys.* 10: 395–409. For illustrative purposes, the impact of material on the moderated $^{252}$Cf neutron spectrum is presented in Table 8. Convolution of various kerma coefficients (see, Caswell, et al., 1982. Kerma factors of elements and compounds for neutron energies below 30 MeV, *Intl. J Appl. Rad. Isot.* 33: 1227–1262) was performed on the moderated neutron energy spectrum in water, A-150 plastic, brain, and muscle at radial distances of 0.5, 1.0, 2.0, and 5.0 cm. The merit of this approach permitted, for example, determination of kerma to muscle in water where the kerma coefficients for muscle were convolved with the moderated $^{252}$Cf neutron energy spectrum in a water phantom. See, Rivard, et al. Calculated variation in neutron spectra for water, brain, and muscle from a $^{252}$Cf point source, in: *American Nuclear Society Radiation Protection and Shielding Division: Technologies for the New Century*, edited by D. T. Ingersoll (ANS Inc., La Grange Park, Ill., 1998), pp. 219–225.

1. AT Neutron Isodose Curves

The parameters necessary for clinical treatment planning with $^{252}$Cf AT sources were determined using the clinical formalism of TG-43, but employing absorbed dose to ICRU 44 muscle instead of to water. As the majority of physical dose from $^{252}$Cf sources is due to neutrons rather than from photons, and since the photon dose component is dependent on phantom size due to moderation of thermal neutrons and subsequent capture primarily through the $^1$H(n, $\gamma$)$^2$H reaction, only the neutron dose component was examined in the development of the present invention.

It should be noted that TG-43 makes no recommendation regarding phantom temperature for dosimetry measurements. While this parameter is unimportant for dosimetry measurements from photon emitting sources, photon emission following thermal neutron capture generally follows a 1/v-type of behavior and is proportional to the inverse-square root of temperature. Thus, an increase of 2.86% may be expected for the thermal neutron capture cross-sections for a change in phantom temperatures from 37° C. to 20° C. This effect is of significant importance to modalities such as neutron capture therapy-enhanced $^{252}$Cf brachytherapy.

The AT encapsulation (Pt/Ir-10%) is more likely to perturb the photon isodose distribution than the neutron isodose distribution. Consequently, reduction of the anisotropy function to unity is not possible for the photon dose component.

Neutron isodose distributions were calculated using a LINUX-based treatment planning program with a reference dose rate per unit source strength of 1.636 cGy/h-µg and a radial dose function fitted to a 5th order polynomial with parameters listed below.

$a_0 = 1.027$;  $a_1 = 2.10 \times 10^{-2}$;
$a_2 = 5.00 \times 10^{-3}$;  $a_3 = 1.50 \times 10^{-3}$;
$a_4 = 2.92 \times 10^{-4}$;  $a_5 = 1.30 \times 10^{-5}$.

Figure 8:
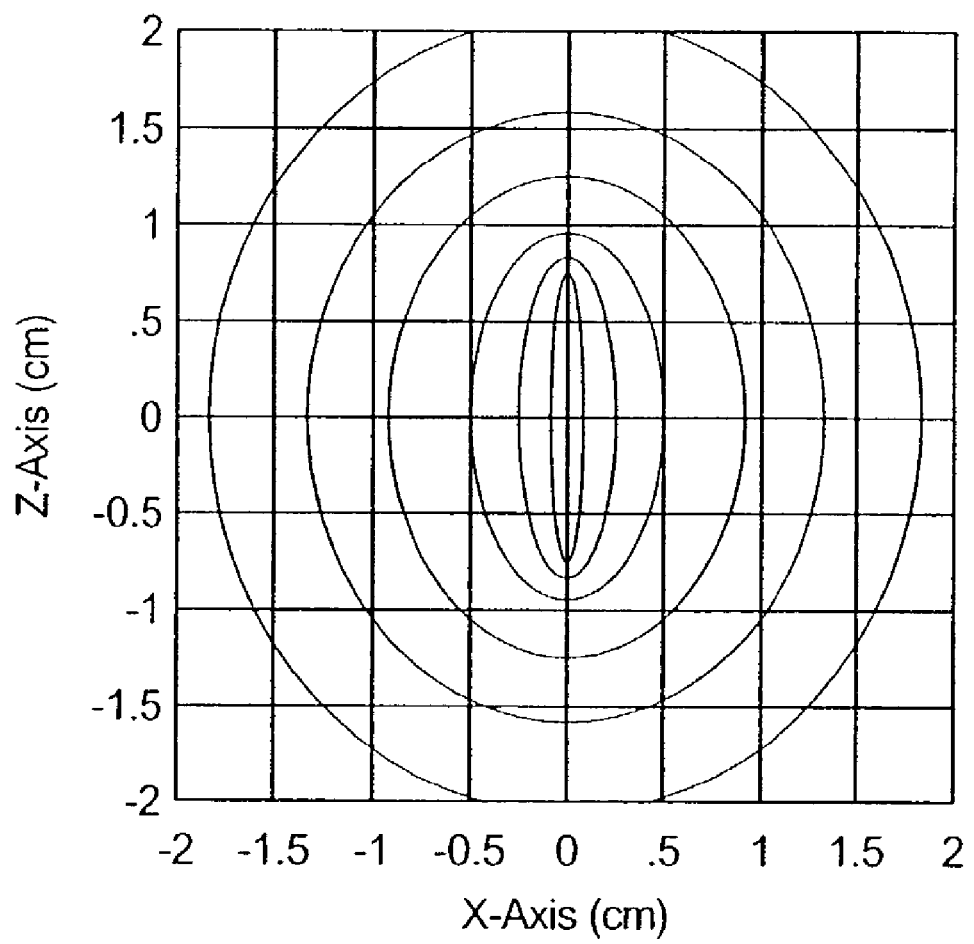
FIG. 8: represents the calculated neutron isodose curves using the recommended parameters for the ORNL-made $^{252}$Cf AT source and the computational results derived from the use of bracketing techniques combined with the van Wijngaarden-Dekker-Brent root finding method (see, Press, et al. Root finding and nonlinear sets of equations," in Numerical Recipes, in: *C: The Art of Scientific Computing* (Cambridge University Press, New York, 1988) pp. 347–393); wherein the neutron dose rates in water starting from the outside isodose curve are: 0.5, 1, 2, 5, 10, and 50 cGy/h-µg.

The radius for a given dose rate and angle was determined using bracketing techniques combined with the van Wijngaarden-Dekker-Brent root finding method. See, Press, et al., Root finding and nonlinear sets of equations," in Numerical Recipes, in: *C: The Art of Scientific Computing* (Cambridge University Press, New York, 1988) pp. 347–393. Calculated neutron isodose curves using the recommended parameters for the ORNL-made $^{252}$Cf AT source and the computational results derived from the use of this program are illustrated in FIG. 8; wherein the neutron dose rates in water starting from the outside isodose curve are: 0.5, 1, 2, 5, 10, and 50 cGy/h-µg. It should be noted that the neutron dose rate in muscle was found to be approximately 14% less than that of water, when using a Watt fission model. See, Rivard, et al., 1999. Clinical brachytherapy with neutron emitting $^{252}$Cf sources and adherence to AAPM TG-43 dosimetry protocol, *Med. Phys.* 26: 87–96. For implementation of results on a commercial treatment planning workstation, a non-linear equation was used to fit the radial dose function where r is in units cm. This form (see, Equation 14) was required of the treatment planning system (Nucletron BPS v. 11.2, Wenendaal, the Netherlands) instead of the 5th order polynomial; however, the difference between the two models was never more than ±2% for radii from 0 to 10 cm with typical differences of less than 0.3%.

$$g(r) = 1.0145 \frac{(1 + 0.0010 r^2)}{(1 + 0.0155 r^2)}. \quad (14)$$

VII. Discussion of the Specific Examples and Experimental Results

Due to moderation of the $^{252}$Cf neutron spectrum, there was a slight dependence on the $W_N/W_C$ ratio and water to muscle kerma ratios as a function of depth. However, these effects for varying depths of 0.5 to 5.0 cm were typically less than 3%. It should be noted that the most significant parameter change was demonstrated in δ. As δ was relatively small, variations of δ by even 40% (i.e., 0.010 to 0.014) caused a shift in total dose calculations of only 0.4%, which was not considered significant. Comparisons between the average total dose measurements with the two IC-17 chambers and the T1 chamber were within 1% for the three common measurement distances of 2.0, 3.0, and 5.0 cm. Interestingly, however, there were significant differences between the results of Colvett et al. (1972. Dose distribution around a $^{252}$Cf needle, *Phys. Med. Biol.* 17: 356–364),  Krishnaswamy (1972. Calculated depth dose tables for $^{252}$Cf sources in tissue, *Phys. Med. Biol.* 17: 56–63), and those values disclosed herein.

A. Comparison of Experimental Measurements with Data of Colvett, et al.

Experimental results obtained herein were compared with measured $^{252}$Cf dosimetry of Colvett, et al. (1972. Dose distribution around a $^{252}$Cf needle, *Phys. Med. Biol.* 17: 356–364). For both the on-axis and off-axis measurements, the total dose measured with the T1 chamber was 11.3%±2.0% less than those values determined by Colvett, et al. However, this discrepancy may be explained when details of each experimental setup are examined (see, Table 9) where many of the parameters used for derivation of total dose are presented.

In a $^{252}$Cf dosimetry review by Anderson (1973. Status of dosimetry for $^{252}$Cf medical neutron sources, *Phys. Med. Biol.* 18: 779–799), many of the differences in experimental setups were initially examined in a quantitative manner. For example, Anderson demonstrated that a 7% dose overestimation in the values determined by Colvett, et al. were due, in part, to the exclusion of $K_{MUSLE}/K_{A-150}$ parameter. An additional discrepancy of 2% was expected when accounting for the difference in the calculated ratio of W/e for neutrons and photons (i.e., 1.057) by both Anderson and Colvett, et al. in comparison to the calculated ratio of W/e disclosed used herein (i.e., 1.080). Finally, an approximate 2% under-estimation in source strength was found to be due to the use of the $^{252}$Cf half-life value (i.e., 2.58 years) by Colvett, et al., rather than the currently accepted value (i.e., 2.645 years). This discrepancy caused the calculation of both the neutron and photon dose rates (i.e., cGy/h-µg) to be approximately 2% high. Upon comparison of the average total dose rates of 0.663, 0.290, 0.164, and 0.103 cGy/h-µg (obtained on-axis at 2.0, 3.0, 4.0, and 5.0 cm using the T1 chamber) of the present invention with the 0.769, 0.337, 0.186, and 0.118 cGy/h-µg average total dose rates derived by of Colvett, et al at the same distance, and by including the aforementioned 11% over-estimation, it becomes evident the ratio of results disclosed herein to those of Colvett, et al were 0.969, 0.967, 0.991 and 0.981 at a distance of 2.0, 3.0, 4.0 and 5.0 cm, respectively. The average of these ratios was calculated to be 0.977. This ratio is considered to be in good agreement due to such factors as: (i) the aforementioned differences in Table 9; (ii) the source strength calibration accuracy (±3%) determined by SRI and ORNL; and (iii) uncertainties in the published guidelines of clinically-acceptable source strength (±3%) set forth in TG-56 (see, Nath, et al. 1997. Code of practice for brachytherapy physics: Report of the AAPM Radiation Therapy Committee Task Group No. 56, *Med. Phys.* 24: 1557–1598). Accordingly, due to the markedly improved measurements of nuclear data used for determination of factors such as $K_{MUSCLE}/K_{A-150}$; $N(E_N)$; and $(W/e)_N/(W/e)_C$, as well as the application of ICRU 45-derived dosimetry formalism, the results disclosed herein have been determined to be significantly more accurate and reliable than those obtained by, for example, Colvett, et al. 1972. Dose distribution around a $^{252}$Cf needle, *Phys. Med. Biol.* 17: 356–364.

B. Comparison of Neutron Dosimetry Results with Krishnaswamy Data

As was the case for the comparison with Colvett et al., there were many differences between the Monte Carlo results obtained herein and those obtained by Krishnaswamy (1972. Calculated depth dose tables for $^{252}$Cf sources in tissue, *Phys. Med. Biol.* 17: 56–63). These differences are presented in Table 10, along with the appropriate correction factors to compare the two calculative studies. It should be noted that a Maxwellian spectrum was utilized in the present invention in the modeling of the $^{252}$Cf neutrons, whereas, in contrast, Krishnaswamy employed a Watt fission spectrum, as illustrated in Equation 15, where E has units MeV.

$$N(E) = \sin h(2E)^{1/2} e^{-0.88E}. \quad (15)$$

Comparison of the moderated neutron kerma in muscle using the Krishnaswamy Watt fission spectra with the kerma determined when using a Maxwellian spectrum, a difference in neutron kerma to muscle was fully expected. For example, at radii of 0.5, 1.0, 2.0, and 5.0 cm, the correction factors used to compare kerma which were calculated by use of the two different neutron energy spectra, were 1.049, 1.050, 1.055, and 1.076, respectively. It should be noted that a specific source strength of $2.34 \times 10^6$ n/s-μg was used (see, Krishnaswamy, 1972. Calculated depth dose tables for $^{252}$Cf sources in tissue, *Phys. Med. Biol.* 17: 56–63), rather than the more recently determined value of $2.314 \; 34 \times 10^6$ n/s-μg (see, Knauer and Martin, Californium-252 production and neutron source fabrication, in: *Californium-252: Isotope for 21st Century Radiotherapy,* edited by J. G. Wierzbicki (Kluwer Academic Publishers, Netherlands, 1997) pp. 7–24), thus necessitating the use of a 1.1% correction factor.

Additionally, as Krishnaswamy modeled an extended (needle) source, L=15 mm, rather than a point source, various geometric factors were required to be examined in order to quantitatively compare the instant invention with the Krishnaswamy study. A simple correction (i.e., 1.029) was applied for the different mass percentages of hydrogen used in the calculations; 10.5% (see, Krishnaswamy, 1972. Calculated depth dose tables for $^{252}$Cf sources in tissue, *Phys. Med. Biol.* 17: 56–63) and 10.3% in the present work.

Finally, excessively large voxels were used near the $^{252}$Cf source where volume averaging within the voxel would markedly decrease the results. See, e.g., Anderson, 1973. Status of dosimetry for $^{252}$Cf medical neutron sources, *Phys. Med. Biol.* 18: 779–799. The use of these corrections on Krishnaswamy's results gave rise to values of 8.3, 2.1, 0.5, and 0.1% for radial distances of 0.5, 1.0, 2.0, and 5.0 cm, respectively. The ratio of MCNP results to those of Krishnaswamy after implementing the corrections of Table 10 were 1.012, 0.969, 0.970, and 1.017 at radii of 0.5, 1, 2, and 5 cm, respectively, or on average 0.992±0.027. This agreement was determined to be within the Monte Carlo uncertainties (i.e., approximately 4%); those uncertainties in the present Monte Carlo calculations are negligible by comparison.

C. Comparison of Calculative Results with Data of Awschalom, et al.

By use of the data presented in Table 7, one may make comparisons of the $^{252}$Cf neutron kerma in a variety of clinically- and radiologically-interesting materials. Due to the higher hydrogen mass content of fat (11.4%) and water (11.1%), respectively, the kermas relative to muscle were significantly larger, 14.5 and 8.3%, respectively, in these two materials. Similarly, the relative hydrogen content of bone (3.4%) and PMMA (8.1%) reduce the neutron kerma to 42.4% and 86.8%, respectively, compared to muscle.

Similarly, by use of Table 7, comparisons may also be made between different neutron sources. See, e.g., Awschalom, et al. 1983. Kerma for various substances averaged over the energy spectra of fast neutron therapy beams: a study in uncertainties, *Med. Phys.* 10: 395–409. Kermas normalized to muscle were arranged in order of increasing average neutron energy. While there were general similarities in relative kermas among the various neutron sources, significant differences (9% and 4% respectively) were also demonstrated between $^{252}$Cf and the external beam sources for pancreas and lung. From ICRU 44 (ICRU Tissue substitutes in radiation dosimetry and measurement, International Commission on Radiation Units and Measurements Bethesda, (ICRU 44, Bethesda, Md., 1989), a 10.6 and 10.3% mass hydrogen content was used for pancreas and lung, respectively. As previously derived, the pancreas and lung compositions were 9.7 and 9.9% mass hydrogen, respectively, as taken from ICRP-23. See, ICRP Report of the task group on Reference Man, International Commission on Radiation Protection, (ICRP-23, Pergamon Press, New York, 1975). These differences in hydrogen content had the correct sign and magnitude, as was expected from the differences in kerma between the neutron sources. It should be noted that the pancreas and lung tissues were the only materials possessing different ICRU 44 and ICRP 23 hydrogen mass content greater than 0.2%. See, ICRU Tissue substitutes in radiation dosimetry and measurement, International Commission on Radiation Units and Measurements Bethesda, (ICRU 44, Bethesda, Md., 1989); ICRP Report of the task group on Reference Man, International Commission on Radiation Protection, (ICRP 23, Pergamon Press, New York, 1975). Also of note are the similarities of neutron kerma for A-150 plastic and brain tissue for the $^{252}$Cf source. Therefore, A-150 plastic may be considered an optimal material with which to measure $^{252}$Cf fast neutron dosimetry in the brain tissue. Additionally, the 5% kerma enhancement between brain and muscle due to a 5% increase in hydrogen content may not be considered detrimental for future applications such as cerebral $^{252}$Cf brachytherapy.

D. Impact of Kerma Coefficients and Phantom Material on Neutron Kerma

Table 8 lists the neutron kerma for various depths in two clinical media and two dosimetry materials. Through comparing data horizontally for all depths, the impact of phantom material on neutron kerma was found to be much less important than choice of kerma coefficients as evidenced in vertical comparisons. By way of example, and not of limitation, at a depth of 1.0 cm, the variation in neutron kerma among the four phantom materials when employing kerma coefficients (see, Anderson, 1986. $^{252}$Cf physics and dosimetry, *Nuc. Sci. App.* 2: 273–281) for muscle was demonstrated to amount to a value of 0.6%. However, when using neutron transport in a muscle phantom and varying the kerma coefficients, the variation then became 3.6%. Even at a depth of 5.0 cm where the $^{252}$Cf neutrons are significantly moderated, the variations were 1.4% and 3.2%, respectively. Consequently, the impact of neutron transport through a given material was shown to be less important than the choice of kerma coefficients.

E. Comparison of Calculated and Experimental Neutron Dose Rates

By use of a 15 mm geometry factor (see, Nath, et al., 1995. Dosimetry of interstitial brachytherapy sources: Recommendations of the AAPM Radiation Therapy Committee Task Group No. 43, *Med. Phys.* 22: 209–234) to compare point source calculations and extended source measurements, the MCNP calculated neutron dose rates may be converted to that for an extended source, such as the AT. This conversion is presented in Table 11 where the ratio of geometry factors for a point source and 15 mm long extended source were 0.9567, 0.9799, 0.9885, and 0.9926 for distances of 2.0, 3.0, 4.0, and 5.0 cm, respectively. See, Rivard, et al. 1999. Clinical brachytherapy with neutron emitting $^{252}$Cf sources and adherence to AAPM TG-43 dosimetry protocol, *Med. Phys.* 26: 87–96. In addition, for comparative purposes, measured neutron rates of AT sources are also presented in Table 11, as are ratios of experimental neutron dose rates to those calculated using MCNP.

From inspection of Table 11, the neutron dose rate as derived using the combination of FWT chambers and GM counter were in approximately the same level of agreement with MCNP results as the neutron dose rate derived using the combination of Exradin chamber and GM counter. The average ratio for the FWT chambers and GM counter combination was 0.989 while the average ratio for the Exradin chamber and GM counter combination was 1.001. Measurements with both chamber combinations agreed with the calculated neutron dose rates at all distances within the uncertainties.

VIII. Encapsulation of Californium-252 for Use in Brachytherapy

While radium-226 ($^{226}$Ra) was traditionally encapsulated with 10% iridium and 90% platinum (Pt/Ir-10%), it is not generally used for clinical treatments. Various medical sources available today are encapsulated in, e.g., titanium, stainless, or nitinol. Prior to the present invention, and as illustrated in FIG. 1, $^{252}$Cf brachytherapy sources have been doubly-encapsulated, giving a rather large external diameter >0.100 inches.

Figure 9:
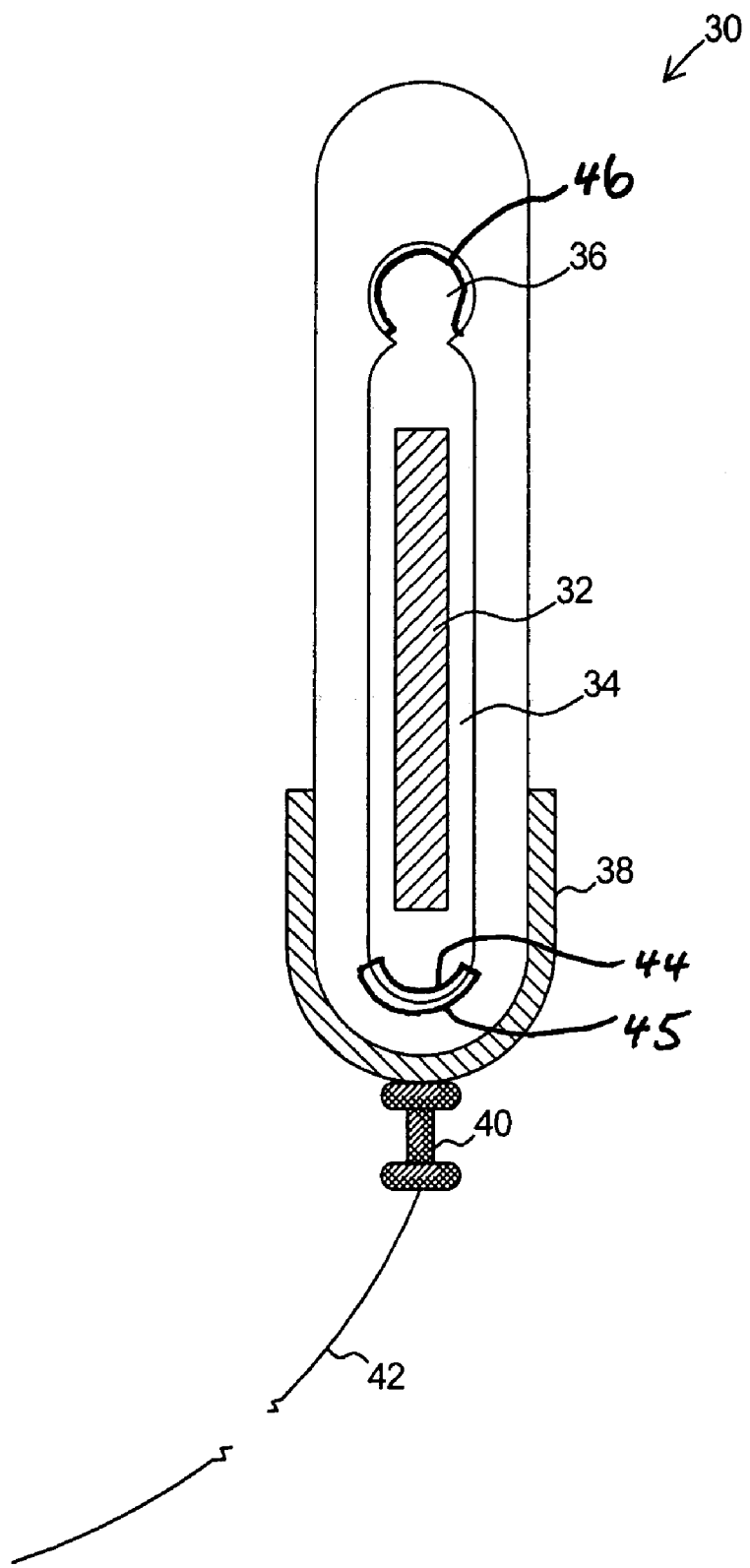
FIG. 9: represents a schematic illustration of the $^{252}$Cf source geometry of the present invention.

In contrast to the prior art AT-based capsule design, the present invention utilizes a $^{252}$Cf encapsulation design which employs single-encapsulation of the source. This capsule is preferably fabricated from a material that is stable thermally and chemically to neutron flux, yet allows the passage of neutrons without obtaining significant radioactivity itself. However, should the capsule material become radioactive by neutron flux, the material and any contaminants of that material should have a short half-life, as compared to the actual radioactive source (i.e., $^{252}$Cf). These materials include, but are not limited to, titanium, stainless steel, nitinol, Pt/Ir-10%, and the zirconium alloy, Zircaloy-2. A schematic illustration of the $^{252}$Cf source geometry 30 of the present invention is shown in FIG. 9. As shown, the geometry 30 includes a radionuclide source 32 disposed in a radionuclide capsule 34 that includes a small cavity 36 for expansion of He gas. The geometry 30 further includes a heat-resistant coating 38 coupled to a connector 40 that is coupled to an afterloader wire 42.

This single-encapsulation methodology of the present invention gives a total external capsular diameter of less-than 0.060 inches, wherein the active diameter ranges from approximately 0.1 to 1.5 mm and a total capsular active length of approximately 3 to 10 mm. Thus, both the diameter and length of the capsule is markedly smaller than the traditional AT-based sources currently used for brachytherapy, which allows greater ability to access extremely small or tight areas within the body (e.g., the brain, blood vessels, etc.).

Unlike for $^{226}$Ra, where concern for capsule leakage is primarily due to production of radon-222 ($^{222}$Rn) gas, the primary gaseous decay product of $^{252}$Cf is helium. Accordingly, the encapsulation design of the present invention specifically includes the incorporation of a small void or cavity at the proximal end of the capsule. This cavity is produced during the manufacturing process by use of an extremely fine drill bit, and allows thermal expansion of the helium to prevent bursting of the capsule. Additionally, layers 44, 45 of ceramic paint are applied to the distal end of the capsule to prevent vaporization of the $^{252}$Cf active source due to thermal transfer when heat-sealing the capsule during the manufacturing process. A layer 46 of ceramic paint is also applied to the proximal end of the capsule.

The concentration of the neutron-emitting $^{252}$Cf source which is used with the encapsulation methodology disclosed by the present invention ranges from approximately 10 µg to 10 mg, with 1 µg of $^{252}$Cf providing a neutron dose of approximately 2,314,000 neutrons/second. Traditional methods for producing $^{252}$Cf sources for encapsulation involve the following steps: (i) the deposition of palladium (Pd) onto $^{252}$Cf oxalate; (ii) the drying and pressing of the mixture in a "green pellet"; (iii) heating of the "green pellet" to approximately 1600° C. to melt the Pd/$^{252}$Cf; and (iv) rolling of the mixture in a jewelry mill to produce a thin wire with a $^{252}$Cf concentration of approximately 500 µg $^{252}$Cf/inch. In contrast, in a preferred embodiment, the present invention discloses the use of $^{252}$Cf oxide (cermet) which is either encapsulated into the aforementioned source capsule of the present invention or is directly sealed into a cavity within the end of a flexible nickel/titanium afterloader wire.

In preferred embodiments of the present invention, the $^{252}$Cf-containing capsule may either be attached to a flexible delivery cable (e.g., a flexible afterloader wire) for subsequent interstitial insertion, or be sealed directly into an end-cavity within a flexible nickel/titanium afterloader wire. In the former example, an intermediate connector with a "dumbbell-shape" is used to attach the sealed source to the delivery cable. The use of this type of connector permits both source handling and decontamination with a convenient means of attachment to the afterloader delivery cable.

Preferably, the afterloader wire is constricted from a material that exhibits little or no memory retention when bent (i.e., can tolerate bending/strain with only a slight alteration in its original shape). Examples of materials that exhibits little or no memory retention when bent include, but are not limited to, Tinel Alloy BB (Raychem Corporation; Menlo Park, Calif.) and Nitinol.RTM (Shape Memory Alloys; Sunnyvale, Calif.). Tinel Alloy BB, Nitinol RTM, and other such nickel/titanium alloys, are comprised of approximately equal quantities of nickel and titanium (e.g., 55% nickel and 45% titanium).

IX. Storage and Delivery of Encapsulated Californium-252 for Use in Brachytherapy For $^{252}$Cf-based High Dose Rate (HDR) brachytherapy, the preferred embodiment of the present invention includes the use of an entire brachytherapy suite which is dedicated to such use and consists of two shielded rooms—a control room and a procedure room. In brief, the $^{252}$Cf brachytherapy suite comprises: (i) a radioactive source storage container or "safe"; (ii) a shielded control area for clinical personnel; (iii) a patient table; and source applicators (e.g., metracolpostats, metrastats, colpostats, rectostats, oesophagostats, and the like).

1. Source Storage Container or "Safe"

Due to size constraints and increased electronic circuit damage by neutrons as compared to photons, a radiation-attenuating source storage container or "safe" which is separate from, and external to, the remote delivery device (i.e., afterloader) is employed in the present invention. Instead of conventional, high-Z materials (e.g., tungsten), a hydrogenous safe is used to attenuate $^{252}$Cf-produced neutrons, and the associated radiation.

Figure 10:
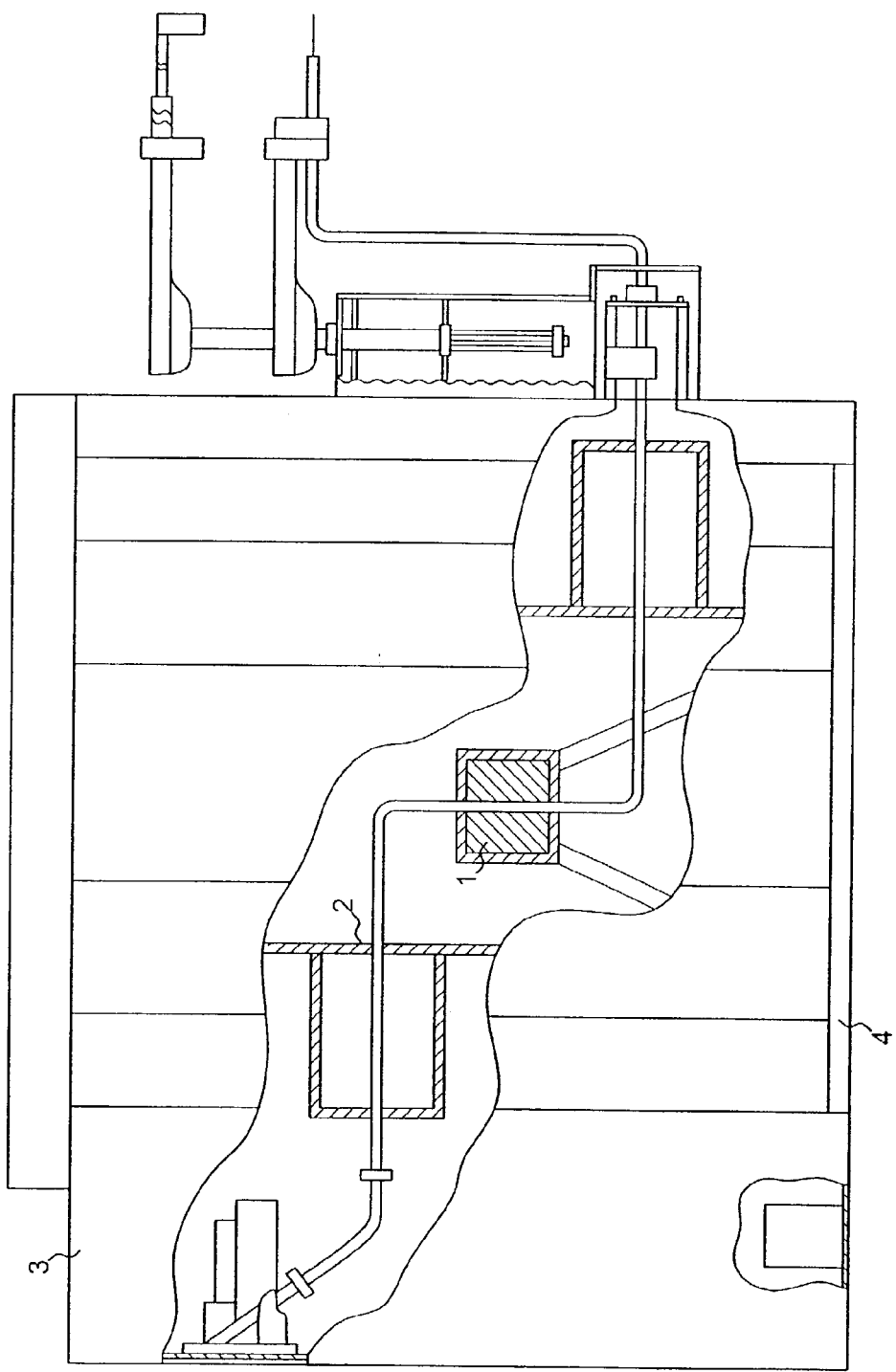
FIG. 10: represents a schematic illustration of the storage container for the $^{252}$Cf source of the present invention.

As illustrated in FIG. 10, the preferred embodiment for the $^{252}$Cf storage container or "safe" of the present invention comprises a total of four layers of various radiation-attenuating materials. The inner-most layer consists of an inner lead cube 1, which serves to attenuate spontaneous and decay products of gamma radiation. The inner lead cube 1 is placed within a double-walled, internal container 2, fabricated from stainless steel or other alloy which is thermally- and chemically-inert to both neutron and gamma radiation. The cavity which formed within the double-walls of the internal container 2 is filled with a neutron-attenuating solution (e.g., a saturated solution of a boric acid or borated polystyrene). The boron-10 ($^{10}B$) isotope within the boric acid solution additionally decreases captured gamma radiation by a factor of approximately 2- to 3-times. The internal container is, itself, then surround by sheets of hydrogenous materials 3 which include, but not limited to, polyethylene, borated-polyethylene, polystyrene, polyester, water-extended polyester, acrylic, nylon rubber, or paraffin, which at at-least approximately 20 cm thick in cross-section. Finally, the sheets of hydrogenous materials 3 are covered by outer sheets of high-Z materials 4, which include, but not limited to, lead, iron, stainless steel, tungsten, bismuth, or depleted uranium, which are at-least approximately 20 mm thick in cross-section, and are sufficient in both size and shape so as to completely enclose the inner lead cube, internal container, and hydrogenous material-enclosure, to additionally protect medical personnel and the patient from hydrogen-captured gamma radiation during patient or source preparation.

Several safety measures are also provided. For example, in contrast to conventional $^{192}Ir$ high dose rate (HDR) remote afterloaders, one of the turret indexes and connecting tubes is dedicated to transfer the $^{252}Cf$ source to an external safe. Also incorporated into the safe is a radiation detector/safety lock which both indirectly measures the $^{252}Cf$ HDR source-strength and alerts clinical personnel and prevents accessing and subsequent delivery of the source should the expected source-strength differs from that of the calculated source-strength (including source decay). Interlocks also prevent the possibility of source extension from the storage container when the procedure room door is open, when the level of the saturated boric acid solution contained within the stainless steel tank is low, or if the source becomes detached from the afterloading wire. In the event of a power failure, additional backup power (through battery or generator) causes retraction of the source into the storage container and saves all information to the computer processor's memory regarding any irradiation which has already been performed on the patient.

2. Afterloader-Based Delivery

Figure 11:
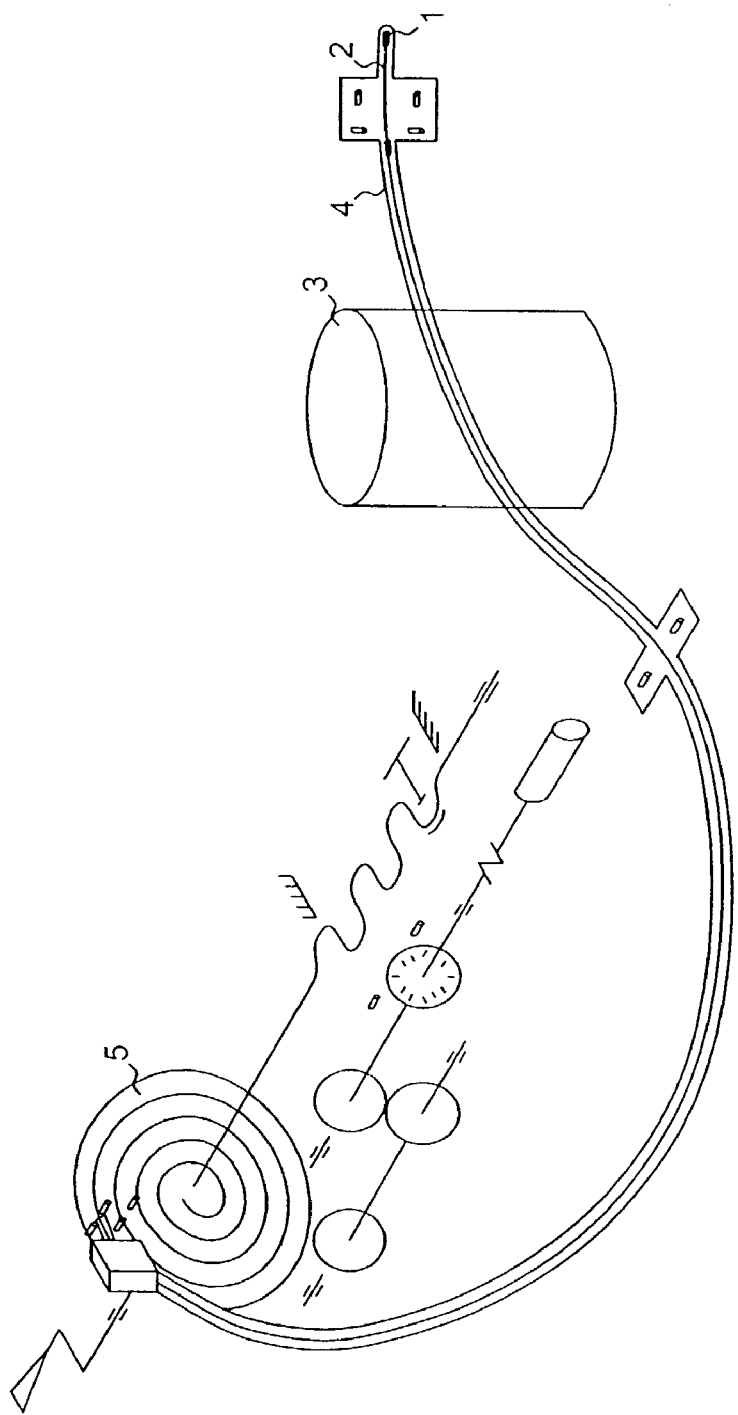
FIG. 11: represents a schematic illustration of the afterloading $^{252}$Cf source delivery device of the present invention.

Due to the high levels of neutron radiation produced by $^{252}Cf$ HDR source, remote delivery and implantation of these sources is employed. This remote delivery/implantation device has been designated an "afterloading device" or "afterloader". The afterloader employed in the practice of the present invention is illustrated in FIG. 11 and comprises: a $^{252}Cf$ source 1; a flexible afterloading wire connected to the source 2; a source storage container or "safe" 3; a flexible, elongated tube for guidance and delivery of the source 4; a stepping motor which moves the flexible afterloading wire and source for delivery 5.

With the afterloading device of the present invention, the source is capable of being moved into a plurality of positions by use of the stepping motor. Thus, the dose distribution to the irradiation volume may be adjusted by variation of both position of the source and dwell time of the source at a specific position. As previously discussed above, there are numerous safety features which are incorporated into the afterloading device of the present invention to prevent delivery of the source in the event of the occurrence of certain anomalous scenarios.

EQUIVALENTS

From the foregoing detailed description of the specific embodiments of the present invention, it should be readily apparent that, for example, unique, improved methodologies for the application of an International Commission on Radiation Units and Measurements (ICRU)-45-like dosimetry protocol to californium-252 ($^{252}Cf$) neutron emitting brachytherapy sources, wherein numerous dosimetry protocol parameters were determined specifically for $^{252}Cf$, as well as novel methods for the encapsulation, storage, and delivery of $^{252}Cf$ sources, have been disclosed herein. Although particular embodiments have been set forth herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

TABLE 1

Measured $N_x$ values for various ionization chambers.

| chamber | IC-17 #1 | IC-17 #2 | T1 |
|---|---|---|---|
| exposure factor (R/nC) | 2.933 ± 0.029 | 3.051 ± 0.031 | 45.53 ± 0.46 |

TABLE 2

$^{252}Cf$ transverse-axis total dose.

| distance (cm) | IC-17 #1 (cGy/h-µg) | IC-17 #2 (cGy/h-µg) | T1 (cGy/h-µg) | Colvett et al. (cGy/h-µg) | Krishnaswamy (cGy/h-µg) |
|---|---|---|---|---|---|
| 1.0 | | | 2.582 | 2.895 | 2.809 |
| 1.5 | | | 1.264 | 1.357 | 1.324 |
| 2.0 | 0.659 | 0.654 | 0.663 | 0.769 | 0.765 |
| 2.5 | | | 0.439 | 0.489 | 0.493 |
| 3.0 | 0.296 | 0.291 | 0.290 | 0.337 | 0.331 |
| 3.5 | | | 0.218 | 0.244 | 0.238 |
| 4.0 | | | 0.164 | 0.186 | 0.179 |
| 4.5 | | | 0.131 | 0.146 | 0.142 |
| 5.0 | 0.102 | 0.099 | 0.103 | 0.118 | 0.112 |

TABLE 3

$^{252}$Cf off-axis total dose.

| position along x away (cm × cm) | T1 (cGy/µg) | Colvett et al. (cGy/h-µg) | Krishnaswamy (cGy/h-µg) |
|---|---|---|---|
| 2.0 × 2.0 | 0.336 | 0.386 | 0.393 |
| 4.0 × 2.0 | 0.128 | 0.143 | 0.140 |
| 2.0 × 4.0 | 0.131 | 0.147 | 0.143 |
| 5.0 × 3.0 | 0.075 | 0.0839 | 0.079 |
| 3.0 × 5.0 | 0.077 | 0.0858 | 0.082 |
| 3.0 × 3.0 | 0.142 | 0.163 | 0.159 |
| 4.0 × 4.0 | 0.080 | 0.0902 | 0.086 |

TABLE 4

Total dose when scanned along the $^{252}$Cf source long-axis.

| position along x away (cm × cm) | T1 (cGy/h-µg) | normalized total dose |
|---|---|---|
| −0.6 × 2.0 | 0.618 | 0.932 |
| −0.4 × 2.0 | 0.645 | 0.973 |
| −0.2 × 2.0 | 0.660 | 0.995 |
| 0.0 × 2.0 | 0.663 | 1.000 |
| 0.2 × 2.0 | 0.655 | 0.989 |
| 0.4 × 2.0 | 0.639 | 0.964 |
| 0.6 × 2.0 | 0.613 | 0.925 |

TABLE 5

$^{252}$Cf AT transverse-axis photon dose.

| distance (cm) | GM-1S (cGy/h-µg) | Colvett et al. (cGy/h-µg) | Krishnaswamy (cGy/h-µg) |
|---|---|---|---|
| 1.0 |  | 0.845 | 0.925 |
| 2.0 | 0.2248 | 0.242 | 0.263 |
| 3.0 | 0.1093 | 0.118 | 0.120 |
| 4.0 | 0.0658 | 0.072 | 0.072 |
| 5.0 | 0.0436 | 0.050 | 0.049 |
| 6.0 | 0.0314 | 0.037 |  |
| 7.0 | 0.0238 |  |  |

TABLE 6

Measured $^{252}$Cf AT transverse-axis neutron dose.

| distance (cm) | (T1) − (GM-1S) (cGy/h-µg) | (IC-17) − (GM-1S) (cGy/h-µg) |
|---|---|---|
| 2.0 | 0.438 | 0.432 |
| 3.0 | 0.181 | 0.184 |
| 4.0 | 0.098 |  |
| 5.0 | 0.059 | 0.0572 |

TABLE 7

$^{252}$Cf neutron kerma at 1 cm, and normalized kerma from other sources.

| | This study | | Awschalom et al. | |
|---|---|---|---|---|
| material | $^{252}$Cf kerma (cGy/h-µg) | $^{252}$Cf kerma muscle' | d(16) + Be muscle' | p(41) + d + T muscle' | Be muscle' |

| material | $^{252}$Cf kerma (cGy/h-µg) | $^{252}$Cf kerma muscle' | d(16) + Be muscle' | p(41) + d + T muscle' | Be muscle' |
|---|---|---|---|---|---|
| muscle | 1.907 ± 0.0011 | 1.000 ± 0.0006 | 1.00 | 1.00 | 1.00 |
| water | 2.064 ± 0.0012 | 1.083 ± 0.0007 | 1.08 | 1.06 | 1.05 |
| brain | 2.009 ± 0.0012 | 1.054 ± 0.0006 | 1.05 | 1.04 | 1.04 |
| skin | 1.910 ± 0.0011 | 1.002 ± 0.0006 | 0.99 | 0.99 | 1.00 |
| blood | 1.928 ± 0.0012 | 1.011 ± 0.0007 | 0.98 | 0.98 | 0.98 |
| fat | 2.183 ± 0.0013 | 1.145 ± 0.0007 | 1.13 | 1.13 | 1.16 |
| pancreas | 1.997 ± 0.0012 | 1.047 ± 0.0006 | 0.96 | 0.97 | 0.96 |
| lung | 1.943 ± 0.0012 | 1.019 ± 0.0006 | 0.97 | 0.98 | 0.98 |
| bone | 0.809 ± 0.0005 | 0.424 ± 0.0003 | 0.44 | 0.52 | 0.52 |
| A-150 | 2.005 ± 0.0012 | 1.053 ± 0.0006 | 1.02 | 1.04 | 1.07 |
| PMMA | 1.654 ± 0.0010 | 0.868 ± 0.0005 | 0.83 | 0.88 | 0.90 |

TABLE 8

$^{252}$Cf neutron kerma (cGy/h-µg) at 0.5, 1.0, 2.0, and 5.0 cm for various phantom materials.

| kerma/radii (cm) | brain phantom | muscle phantom | water phantom | A-150 phantom |
|---|---|---|---|---|
| brain 0.5 | 8.054 | 8.070 | 8.038 | 8.107 |
| muscle 0.5 | 7.613 | 7.628 | 7.598 | 7.664 |
| water 0.5 | 8.311 | 8.327 | 8.295 | 8.366 |
| A-150 0.5 | 7.956 | 7.971 | 7.941 | 8.007 |
| brain 1.0 | 2.009 | 2.016 | 2.001 | 2.031 |
| muscle 1.0 | 1.900 | 1.907 | 1.892 | 1.921 |
| water 1.0 | 2.072 | 2.080 | 2.064 | 2.095 |
| A-150 1.0 | 1.984 | 1.992 | 1.977 | 2.005 |
| brain 2.0 | 0.483 | 0.487 | 0.480 | 0.490 |
| muscle 2.0 | 0.457 | 0.461 | 0.454 | 0.464 |
| water 2.0 | 0.497 | 0.502 | 0.495 | 0.505 |
| A-150 2.0 | 0.477 | 0.481 | 0.474 | 0.484 |
| brain 5.0 | 0.0591 | 0.0607 | 0.0591 | 0.0588 |
| muscle 5.0 | 0.0561 | 0.0576 | 0.0561 | 0.0558 |
| water 5.0 | 0.0605 | 0.0623 | 0.0606 | 0.0602 |
| A-150 5.0 | 0.0584 | 0.0600 | 0.0585 | 0.0581 |

TABLE 9

Experimental parameters of Colvett et al. and present study.

| parameter | Colvett et al. | This study (IC-17 and T1) |
|---|---|---|
| phantom size | 0.200 m$^3$ | 0.054 m$^3$ |
| phantom composition | 0.109 g/cm$^3$ H | 0.112 g/cm$^3$ H |
|  | 0.13 g/cm$^3$ C | 0.888 g/cm$^3$ O |
|  | 0.79 g/cm$^3$ O |  |
| phantom temperature | 22° C.? | 18° C. |
| chamber volume(s) | 0.0018 cm$^3$ | 1.0 and 0.05 cm$^3$ |
| chamber wall thickness | 3.4 mm | 4.1 mm |
| detector type | proportional counter | ionization chamber |
| chamber fill gas | 55% C$_3$H$_8$, | 63.84% CH$_4$, |
|  | 39.6% CO$_2$, | 32.97% CO$_2$, |
|  | 5.4% N$_2$ | 3.19% N$_2$ |
| (W/e)$_N$/(W/e)$_C$ | 1.057 | 1.080 |
| K$_{MUSCLE}$/K$_{A-150}$ | not included | 0.958 |
| ($\mu_{en}/\rho$)$_{MUSCLE}$/($\mu_{en}/\rho$)$_{A-150}$ | not included | 1.001 |
| d$_r$ | not included | 1.000 |
| A$_{WALL}$ | not included | 0.983 and 0.992 |
| source strength | ~5 µg | 326.23 µg |
| source type | needle | Applicator Tube |
| half-life | 2.58 | 2.645 |
| source arrangement | along-away (gradient) | cylindrical symmetry (uniform) |

TABLE 10

Calculative parameters of Krishnaswamy and present study.

| parameter | Krishnaswamy | This study | correction factor 0.5, 1.0, 2.0, 5.0 cm |
|---|---|---|---|
| $^{252}$Cf source spectrum | Watt fission | Maxwellian | 1.049, 1.050, 1.055, 1.076 |
| specific $^{252}$Cf strength | $2.34 \times 10^6$ n/s-µg | $2.314 \times 10^6$ n/s-µg | 1.011, 1.011, 1.011, 1.011 |
| $^{252}$Cf source geometry | needle | point | 0.655, 0.858, 0.957, 0.993 |
| $^1$H proportion | 10.5% | 10.2% | 1.029, 1.029, 1.029, 1.029 |
| voxel bin spacing | 0.50 cm | 0.01 cm | 1.083, 1.021, 1.005, 1.001 |

TABLE 11

$^{252}$Cf AT transverse-axis neutron dose rate.

| distance (cm) | (T1) - (GM-1S) (cGy/ h-µg) | (IC-17) - (GM-1S) (cGy/ h-µg) | MCNP (cGy/h-µg) | (T1) - (GM-1S) ratio to MCNP | (IC-17) - (GM-1S) ratio to MCNP |
|---|---|---|---|---|---|
| 2.0 | 0.438 ± 0.021 | 0.432 ± 0.011 | 0.44030 ± 0.00035 | 0.995 ± 0.050 | 0.982 ± 0.025 |
| 3.0 | 0.181 ± 0.009 | 0.184 ± 0.005 | 0.18764 ± 0.00017 | 0.965 ± 0.048 | 0.981 ± 0.025 |
| 4.0 | 0.098 ± 0.005 | | 0.097809 ± 0.00011 | 1.002 ± 0.050 | |
| 5.0 | 0.059 ± 0.003 | 0.057 ± 0.001 | 0.056656 ± 0.000068 | 1.041 ± 0.052 | 1.005 ± 0.025 |

TABLE 12

Application of Monte Carlo transport physics (MB (14B)) using PVM.

| computer | processor type clock speed | operating system | PVM speed weighting | PVM hierarchy |
|---|---|---|---|---|
| sgi_1 | R3000 MIPS 33 Mhz | IRIX 5.2 | 200 | slave |
| sgi_2 | R4000 MIPS 132 MHz | IRIX 4.0.5F | 1000 | slave |
| sgi_3 | R4000 MIPS 132 MHz | IRIX 4.0.5F | 1000 | slave |
| sgi_4 | R4000 MIPS 132 MHz | IRIX 4.0.5F | 1000 | slave |
| pc25 | 86486DX 100 MHz | LINUX 2.0.27 | 500 | slave |
| pc93 | P2 266 MHz | LINUX 2.0.27 | 5000 | master |

TABLE 13

Dose calibrator measurements of 12 SRL-made AT sources.

| SRL-made AT serial # | source strength (µg) | dose calibrator (Rdg) | ratio (µg/ Rdg) | SRL-made AT serial # | source strength (µg) | dose calibrator (Rdg) | ratio (µg/ Rdg) |
|---|---|---|---|---|---|---|---|
| AT-309 | 6.651 | 6.62 | 1.005 | AT-315 | 6.463 | 6.48 | 0.997 |
| AT-310 | 6.633 | 6.63 | 1.000 | AT-316 | 6.387 | 6.37 | 1.003 |
| AT-311 | 6.662 | 6.66 | 1.000 | AT-317 | 6.592 | 6.61 | 0.997 |
| AT-312 | 6.423 | 6.44 | 0.997 | AT-318 | 6.687 | 6.71 | 0.997 |
| AT-313 | 6.645 | 6.61 | 1.005 | AT-319 | 6.519 | 6.54 | 0.997 |
| AT-314 | 6.472 | 6.46 | 1.002 | AT-320 | 6.477 | 6.45 | 1.004 | avg. ratio (µg/Rdg) = 1.000
ratio range +0.5%, −0.3%
ratio variation (I σ) = 0.3%

TABLE 14

Dose calibrator measurements of 13 ORNL-made AT sources.

| ORNL-made AT serial # | source strength (µg) | dose calibrator (Rdg) | ratio (µg/ Rdg) | ORNL-made AT serial # | source strength (µg) | dose calibrator (Rdg) | ratio (µg/ Rdg) |
|---|---|---|---|---|---|---|---|
| AT-321 | 27.77 | 27.7 | 1.003 | AT-328 | 27.41 | 27.4 | 1.000 |
| AT-322 | 28.24 | 28.3 | 0.998 | AT-329 | 27.57 | 27.6 | 0.999 |
| AT-323 | 26.94 | 26.9 | 1.001 | AT-330 | 25.59 | 25.6 | 0.997 |
| AT-324 | 28.43 | 28.3 | 1.005 | AT-331 | 26.44 | 26.4 | 1.002 |
| AT-325 | 28.71 | 28.8 | 0.997 | AT-332 | 27.38 | 27.3 | 1.003 |
| AT-326 | 26.19 | 26.3 | 0.996 | AT-333 | 26.46 | 26.3 | 1.006 |
| AT-327 | 26.29 | 26.2 | 1.003 | | | | | avg. ratio (µg/Rdg) = 1.001
ratio range +0.6%, −0.4%
ratio variation (I σ) = 0.3%

What is claimed is:

1. A device for the encapsulation of radionuclides for use in brachytherapy, comprising:

a generally cylindrical, elongated capsule, constructed of a material which is chemically- and thermally-stable to both neutron and gamma radiation, having a contiguous outer surface, an internal cavity to accommodate buildup of helium gas following alpha decay by californium-252, a distal end, and a proximal end, wherein a surface of either end of said capsule is coated with a substantially thermally non-conductive coating; and a means for emitting radioactivity, said radioactive means localized within said internal cavity of said capsule, wherein said proximal end and said distal end of said capsule are sealed to prevent the release of said radioactive means.

2. The device of claim 1, wherein said radioactive means is a neutron-emitting radionuclide.

3. The device of claim 1, wherein said radioactive means is the neutron-emitting radionuclide californium-252.

4. The device of claim 1, wherein the concentration of said californium-252 source ranges from approximately 1 µg to 10 mg.

5. The device of claim 1, wherein an encapsulation diameter of said capsule ranges from approximately 0.1 mm to 1.5 mm and an encapsulation length of said capsule ranges from approximately 3 mm to 20 mm.

6. The device of claim 1, wherein said capsule is fabricated from a material selected from the group consisting of: stainless steel, titanium, nickel/titanium alloy, Zircaloy-2, nitinol, aluminum 1100, and an alloy comprising approximately 90% platinum and 10% iridium.

7. The device of claim 1, wherein the substantially thermally non-conductive coating comprises a ceramic paint.

8. The device of claim 1, wherein the shape and total dimensions of said capsule are such that it is capable of passing through the interior of a hollow tube or needle, and wherein the interior diameter of said hollow tube or needle ranges from approximately 20 gauge to approximately 12 gauge.

9. The device of claim 1 further comprising:
a coupling means secured to said proximal end of said capsule, wherein said coupling means is used to attach said capsule to a flexible wire, essentially circular in cross-section, having a first and second end, wherein said second end of said flexible wire is attached to said coupling means; and
a hollow, generally-cylindrical, elongated tube having an exterior surface, an interior surface, and a first and second end, and an original configuration, said elongated tube constructed of a material that can withstand flexation without permanent alteration in said elongated tube's original configuration, and wherein said elongated tube has an internal diameter sufficient to allow passage of said capsule, said coupling means, and said flexible wire therethrough.

10. An encapsulated radionuclide source, for use in a method of brachytherapy treatment comprising administration of the encapsulated radionuclide source to an individual in need thereof, comprising:
a generally cylindrical, elongated capsule, constructed of a material which is chemically- and thermally-stable to both neutron and gamma radiation, having a contiguous outer surface, a large internal cavity with a contiguous inner surface, a small internal cavity with a contiguous inner surface which is connected to said large internal cavity by an elongated cylindrical passageway, a distal end, and a proximal end, wherein a surface of said distal end of said capsule is coated with a coating configured to substantially prevent thermal transfer; and
a means for emitting radioactivity, said radioactive means localized within said internal cavity of said capsule, wherein said proximal end and said distal end of said capsule are sealed to prevent the release of said radioactive means.

11. The source of claim 10, wherein said radioactive means is a neutron-emitting radionuclide.

12. The source of claim 10, wherein said radioactive means is the neutron-emitting radionuclide californium-252.

13. The source of claim 12, wherein the concentration of said californium-252 source ranges from approximately 1 µg to 10 mg.

14. The source of claim 10, wherein the active diameter of said capsule ranges from approximately 0.1 mm to 1.5 mm and the active length of said capsule ranges from approximately 3 mm to 10 mm.

15. The source of claim 10, wherein said capsule is fabricated from a material selected from the group consisting of: stainless steel, titanium, nickel/titanium alloy, Zircaloy-2, nitinol, aluminum 1100, and an alloy comprising approximately 90% platinum and 10% iridium.

16. The source of claim 10, wherein the coating comprises a ceramic paint.

17. The source of claim 10, wherein the shape and total dimensions of said capsule are such that it is capable of passing through the interior of a hollow tube or needle, and wherein the interior diameter of said hollow tube or needle ranges from approximately 20 gauge to approximately 12 gauge.

18. The source of claim 10, wherein the encapsulated radionuclide source further comprises:
a coupling means secured to said distal end of said capsule, wherein said coupling means is used to attach said capsule to a flexible wire, essentially circular in cross-section, having a first and second end, wherein said second end of said flexible wire is attached to said coupling means; and
a hollow, generally-cylindrical, elongated tube having an exterior surface, an interior surface, and a first and second end, and an original configuration, said elongated tube constructed of a material that can withstand flexation without permanent alteration in said elongated tube's original configuration, and wherein said elongated tube has an internal diameter sufficient to allow passage of said capsule, said coupling means, and said flexible wire therethrough.

19. A device for encapsulation of radionuclides for use in brachytherapy, the device comprising:
a substantially cylindrical, elongated capsule, of a material that is substantially chemically and thermally stable to both neutron and gamma radiation, the capsule including a distal end and a proximal end, with at least one of the ends having a surface of a material configured to substantially prevent heat transfer, the capsule having a contiguous outer surface and defining an internal cavity shaped to accommodate gas buildup, the capsule being configured to retain the gas; and
radioactive means for emitting radioactivity, the radioactive means being localized within the internal cavity of the capsule,
wherein the proximal end and the distal end of the capsule are substantially sealed to inhibit the release of the radioactive means.

20. The device of claim 19 wherein the radioactive means is a neutron-emitting radionuclide.

21. The device of claim 20 wherein the radioactive means is the neutron-emitting radionuclide californium-252.

22. The device of claim 21 wherein a concentration of the californium-252 source is within a range from approximately 1 µg to approximately 10 mg.

23. The device of claim 19, wherein an encapsulation diameter of the capsule is between approximately 0.1 mm and about 1.5 mm and an encapsulation length of the capsule is between approximately 3 mm and approximately 20 mm.

24. The device of claim 19 wherein the capsule is fabricated from a material selected from the group consisting of: stainless steel, titanium, nickel/titanium alloy, Zircaloy-2, nitinol, aluminum 1100, and an alloy comprising approximately 90% platinum and approximately 10% iridium.

25. The device of claim 19 wherein the inner surface comprises a coating of a ceramic paint.

26. The device of claim 19 wherein the capsule is shaped and sized to pass through an interior of a hollow tube or needle, and wherein an interior diameter of the hollow tube or needle is in a range from approximately 20 gauge to approximately 12 gauge.

27. The device of claim 19 further comprising:
a coupling means secured to the proximal end of the capsule, the coupling means being configured to attach the capsule to a flexible wire, essentially circular in cross-section, having a first wire end and a second wire end, the second wire end being attached to the coupling means; and
a hollow, generally-cylindrical, elongated tube having an exterior surface, an interior surface, a first tube and second tube end, and an original configuration, the elongated tube being of a material that can withstand flexing without substantial permanent alteration in the original configuration, the tube having an internal diameter sufficient to allow passage of the capsule, the coupling means, and the flexible wire therethrough.

28. The device of claim 19 wherein the surface of the at least one of the ends of the capsule is configured to inhibit conductive heat transfer.

29. A device for encapsulation of radionuclides for use in brachytherapy, the device comprising:

a substantially cylindrical, elongated capsule, including a material that is substantially chemically and thermally stable to both neutron and gamma radiation, with a surface of an end of the capsule being configured to substantially prevent conductive heat transfer, the cap sule having a contiguous outer surface and defining an internal cavity shaped to accommodate gas buildup; and a radioactive element configured to emit radioactivity and being localized within the internal cavity of the capsule;

wherein ends of the capsule are substantially sealed to inhibit the release of the radioactive element; and wherein the surface of the end of the capsule includes a substantially thermally non-conductive coating.

* * * * *